US012692215B2

(12) United States Patent
Turón Dols et al.

(10) Patent No.: US 12,692,215 B2
(45) Date of Patent: Jul. 28, 2026

(54) PROCESS FOR PRODUCING FUNCTIONALIZED ORGANIC MOLECULES AND USES THEREOF

(71) Applicant: Universitat Politècnica de Catalunya, Barcelona (ES)

(72) Inventors: Pau Turón Dols, Rubí (ES); Vanesa Sanz Beltrán, Rubí (ES); Anna Maria Rodríguez Rivero, Rubí (ES); Carlos Enrique Alemán Llansó, Barcelona (ES); Jordi Puiggalí Bellalta, Badalona (ES); Guillem Revilla-López, Barcelona (ES); Jordi Sans, Barcelona (ES)

(73) Assignee: Universitat Politécnica de Catalunya, Barcelona (ES)

( * ) Notice: Subject to any disclaimer, the term of this patent is extended or adjusted under 35 U.S.C. 154(b) by 778 days.

(21) Appl. No.: 17/921,755

(22) PCT Filed: Apr. 27, 2021

(86) PCT No.: PCT/EP2021/060996
§ 371 (c)(1),
(2) Date: Oct. 27, 2022

(87) PCT Pub. No.: WO2021/219644
PCT Pub. Date: Nov. 4, 2021

(65) Prior Publication Data
US 2023/0159417 A1 May 25, 2023

(30) Foreign Application Priority Data

Apr. 28, 2020 (EP) .................................... 20382345
Oct. 21, 2020 (EP) .................................... 20382918

(51) Int. Cl.
$C07C\ 29/159$ (2006.01)
$B01D\ 53/86$ (2006.01)
(Continued)

(52) U.S. Cl.
CPC ........ $C07C\ 29/159$ (2013.01); $B01D\ 53/8671$ (2013.01); $B01J\ 27/1806$ (2013.01);
(Continued)

(58) Field of Classification Search
CPC ....... C07C 29/159; C07C 45/66; C07C 51/15; B01D 53/8671; B01D 2255/2045;
(Continued)

(56) References Cited

U.S. PATENT DOCUMENTS

2008/0220489 A1 9/2008 Offerman
2009/0056204 A1 3/2009 Tsuchida et al.
(Continued)

FOREIGN PATENT DOCUMENTS

EP 3278818 A1 2/2018
EP 3321230 A1 5/2018
(Continued)

OTHER PUBLICATIONS

Practical Process & Research Development, 2000, pp. 12 and 169 (Anderson) (Year: 2000).*
(Continued)

*Primary Examiner* — Amy C Bonaparte
*Assistant Examiner* — Derek Rhoades
(74) *Attorney, Agent, or Firm* — Hayes Soloway, PC

(57) ABSTRACT

A process for producing functionalized organic molecules having 1 to 3 carbon atoms. The method includes the step of contacting carbon dioxide as the only gas, or a gas mixture
(Continued)

that includes carbon dioxide and methane, in the presence of water, with a catalyst that includes permanently polarized hydroxyapatite.

18 Claims, 14 Drawing Sheets

(51) Int. Cl.

| | |
|---|---|
| *B01J 27/18* | (2006.01) |
| *B01J 37/08* | (2006.01) |
| *B01J 37/34* | (2006.01) |
| *C07C 45/66* | (2006.01) |
| *C07C 51/15* | (2006.01) |

(52) U.S. Cl.
CPC .............. *B01J 37/08* (2013.01); *B01J 37/342* (2013.01); *C07C 45/66* (2013.01); *C07C 51/15* (2013.01); *B01D 2255/2045* (2013.01); *B01D 2255/20715* (2013.01); *B01D 2255/806* (2013.01); *B01D 2257/504* (2013.01)

(58) Field of Classification Search
CPC .... B01D 2255/20715; B01D 2255/806; B01D 2257/504; B01J 27/1806; B01J 37/08; B01J 37/342
See application file for complete search history.

(56) References Cited

U.S. PATENT DOCUMENTS

| | | |
|---|---|---|
| 2010/0105118 A1 | 4/2010 | Bell |
| 2014/0090972 A1 | 4/2014 | O'Connor et al. |

FOREIGN PATENT DOCUMENTS

| | | |
|---|---|---|
| JP | 2017178915 A | 10/2017 |
| WO | 2009028166 A1 | 3/2009 |
| WO | 2018024727 A1 | 2/2018 |

OTHER PUBLICATIONS

Product Description, pp. 1-3; published Nov. 5, 2012 (Heraeus) (Year: 2012).*

Chem. Rev. 2019, 119, 7610-7672 (Nipoti et al.) (Year: 2019).*

Rivas et al., "Sustainable synthesis of amino acids by catalytic fixation of molecular dinitrogen and carbon dioxide," Green Chemistry, Sep. 26, 2017, 9 pages.

Search Report received in International Application No. PCT/EP2021/060996 dated Jun. 11, 2021, 4 pages.

Written Opinion received in International Application No. PCT/EP2021/060996 dated Jun. 11, 2021, 5 pages.

An et al., "Cooperative cooper centres in a metal-organic framework for selective conversion of CO2 to ethanol," Nature Catalysis, vol. 2, Aug. 2019, 9 pages.

Liu et al., "Highly Active, Durable Ultrathin MoTe2 Layers for the Electroreduction of CO2 to CH4," Electrocatalysts, small, 2018, [no date], 7 pages.

Liu et al., "Water splitting-biosynthetic system with CO2 reduction efficiencies exceeding photosynthesis," Bioenergy, Jun. 3, 2016, vol. 352, Issue 6290, 5 pages.

Power, "Main-group elements as transition metals," Nature, vol. 463, Jan. 14, 2010, 7 pages.

Wang et al., "Direct synthesis of ethanol via CO2 hydrogenation using supported gold catalysts," ChemComm, 2016, 52, Nov. 14, 2016, 14 pages.

Weetman et al., "The Road Travelled: After Main-Group Elements as Transition Metals," ChemCatChem, 2018, 10, Aug. 24, 2018, 16 pages.

Wiedner et al., "Making a Splash in Homogeneous CO2 Hydrogenation: Elucidating the Impact of Solvent on Catalytic Mechanisms," Chemistry a European Journal, Chem. Eur. J. Jul. 27, 2018, 8 pages.

Yeung, "Photoredox Catalysis as a Strategy for CO2 Incorporation: Direct Access to Carboxylic Acids from a Renewable Feedstock," Wiley Online Library, Angew. Chem. Int. Ed, 2019, Feb. 21, 2019, 11 pages.

Zhu et al., "Recent Advances in Inorganic Heterogeneous Electrocatalysts for Reduction of Carbon Dioxide," Adv. Mater, 2016, 28, Mar. 21, 2016, 30 pages.

Wenjun Zhang, "Progress and Perspective of Electrocatalytic CO2 Reduction for Renewable Carbonaceous Fuels and Chemicals", Article, 2018, 1-24, vol. 5, No. 1700275, Advanced Science.

* cited by examiner

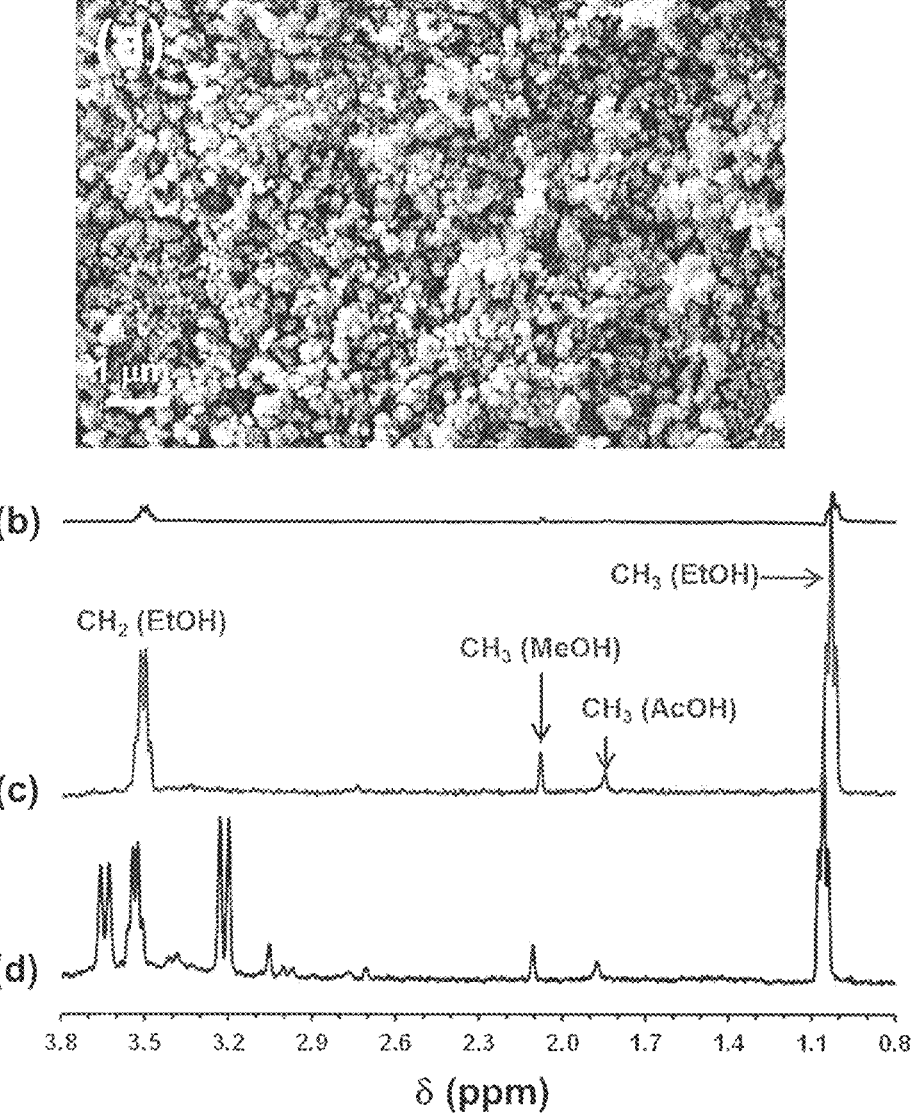
Fig. 3(a)-(d)

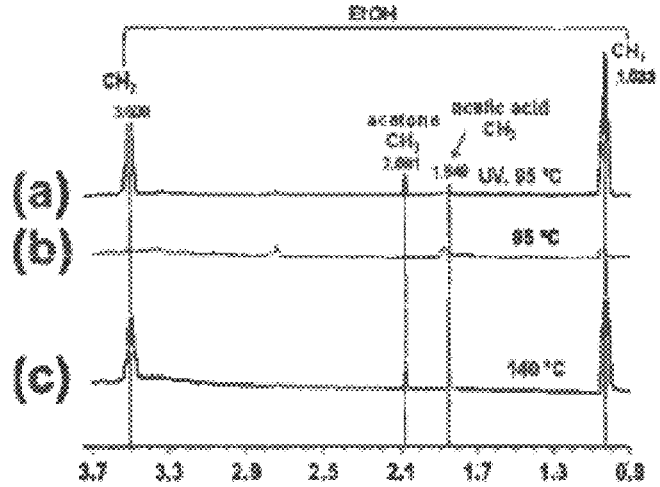
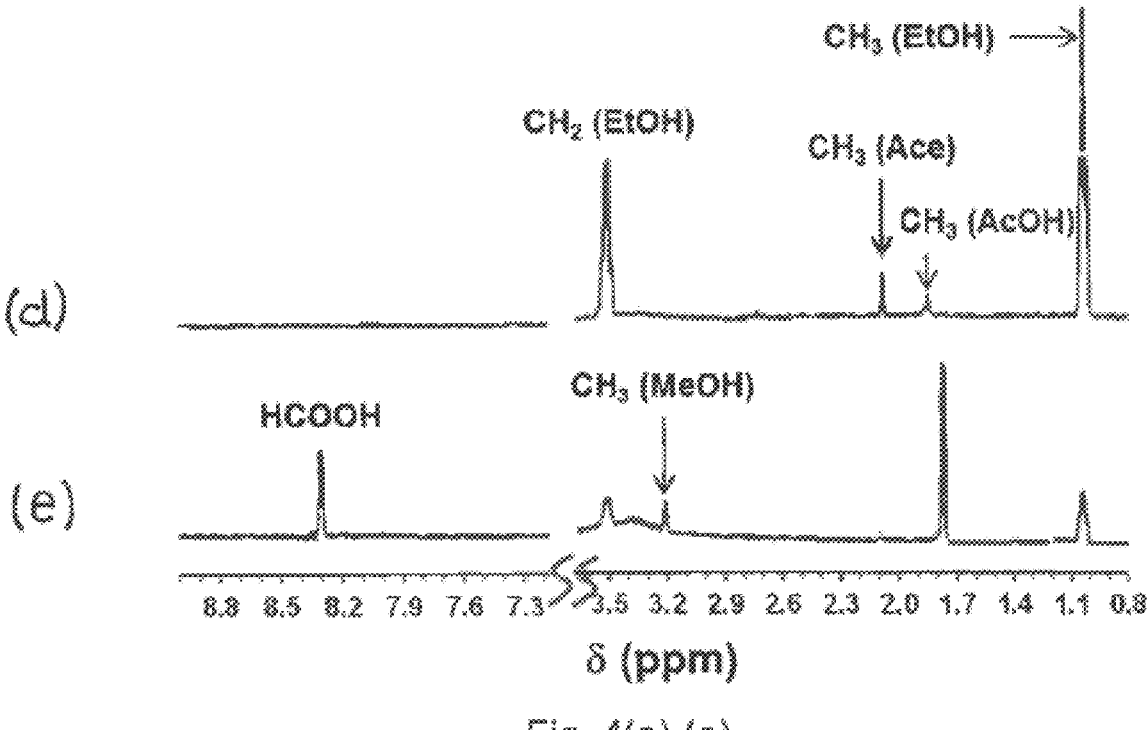
Fig. 4(a)-(e)

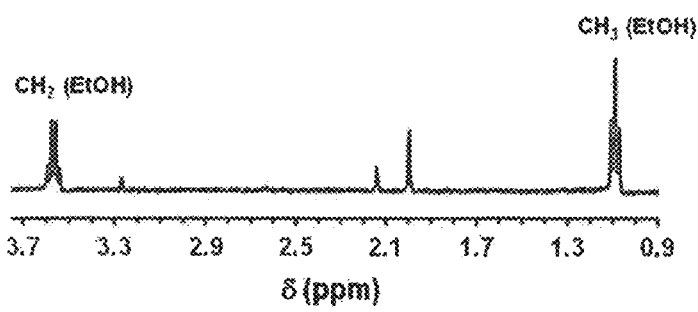
Fig. 10
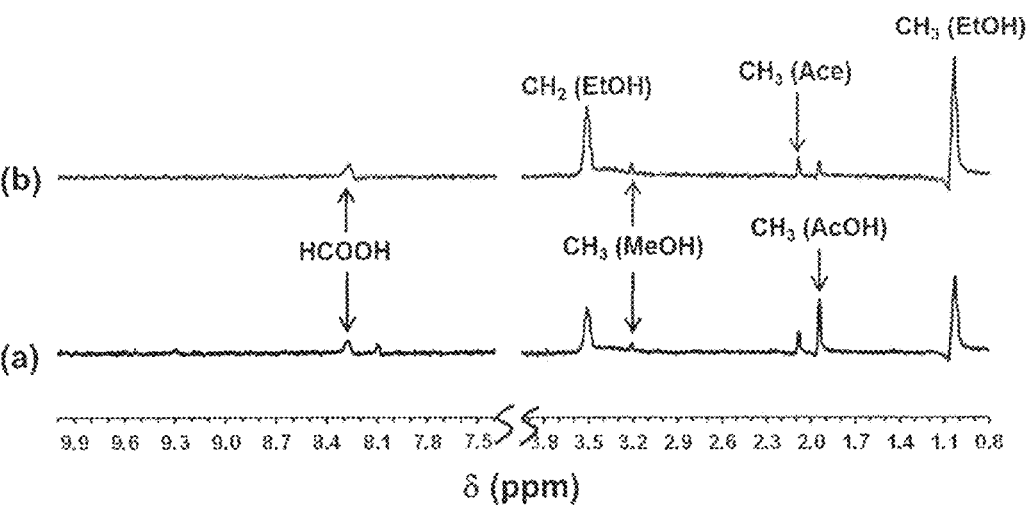
FIG. 11(a)-(b)

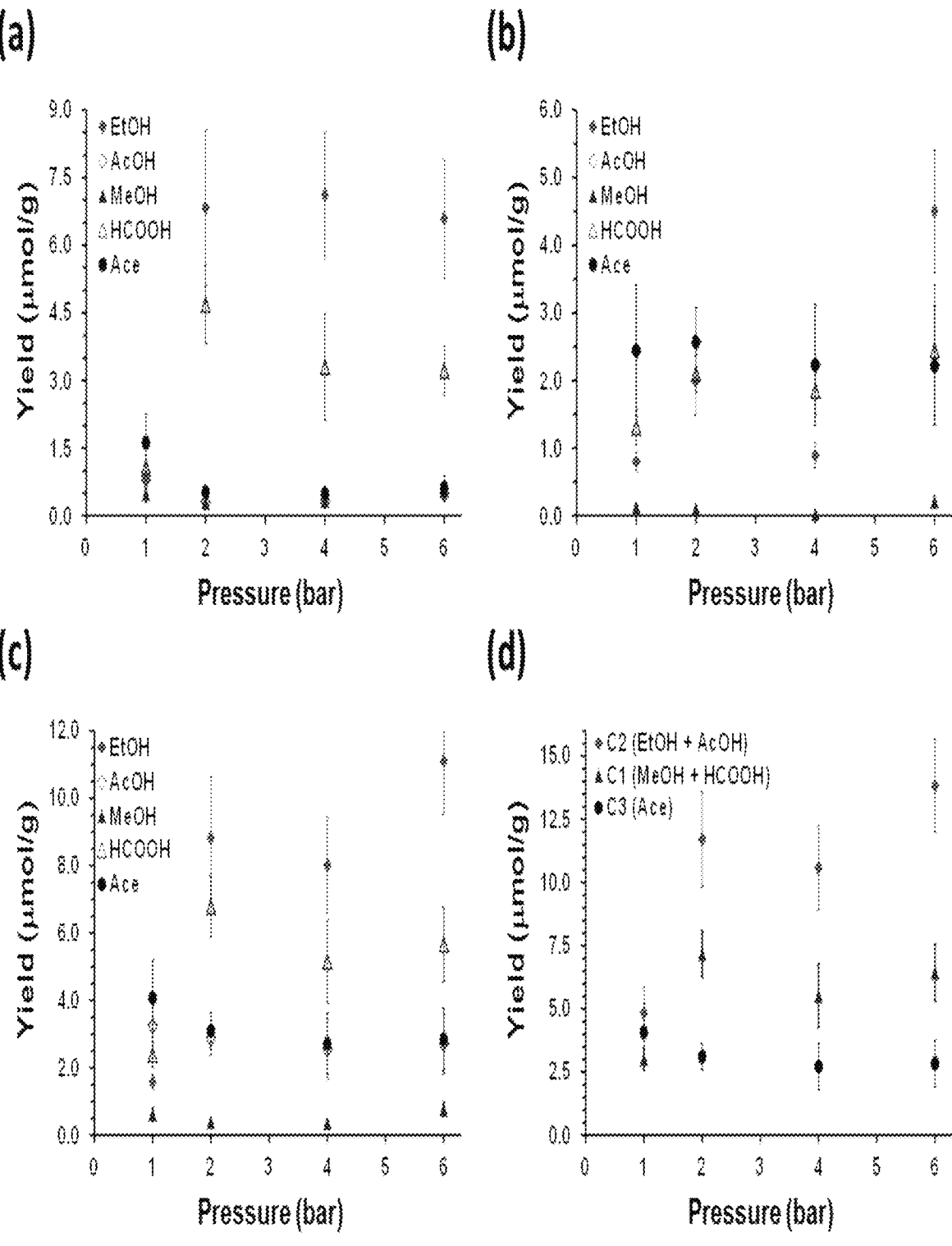
Fig. 12(a)-(d)

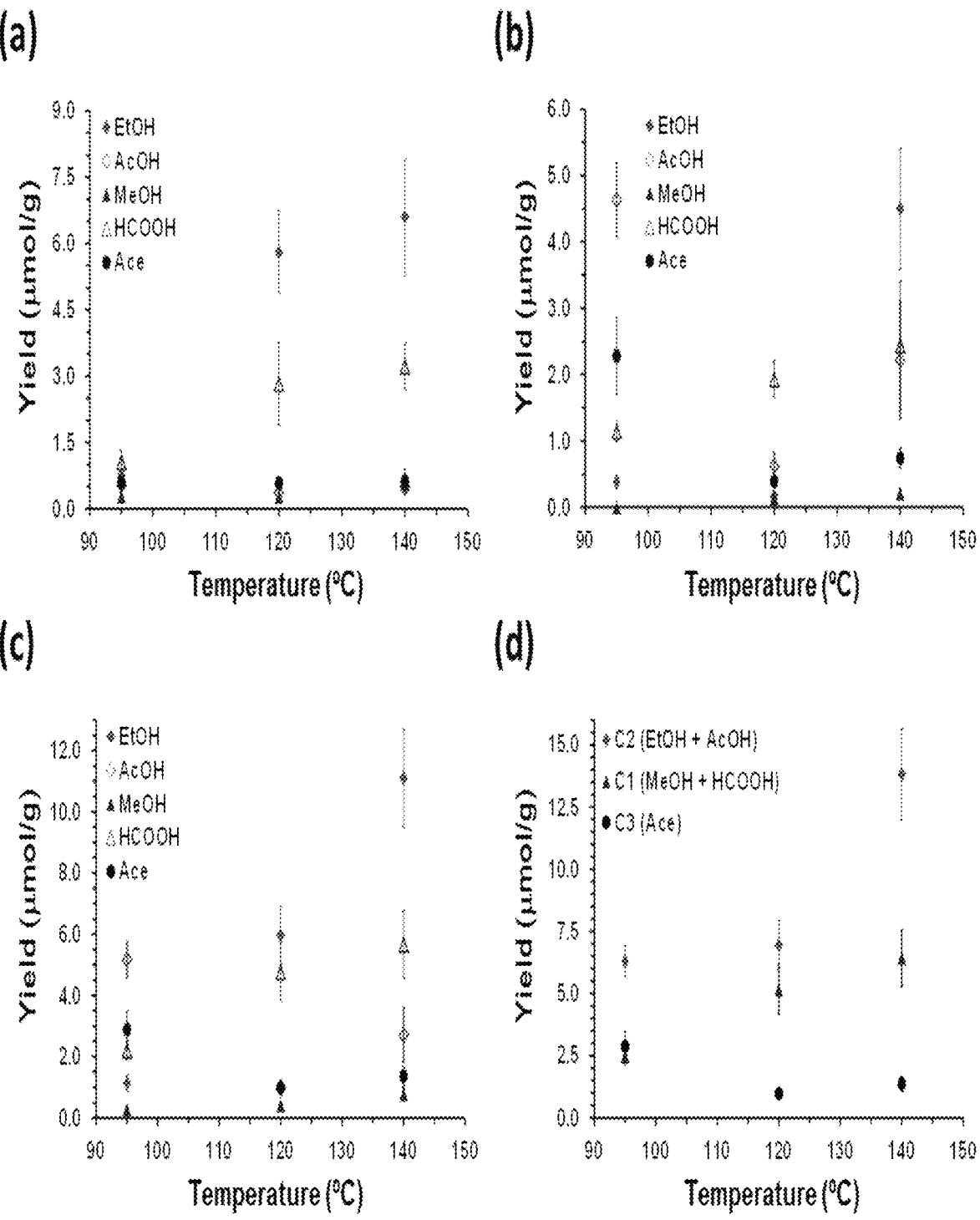
Fig. 13(a)-(d)

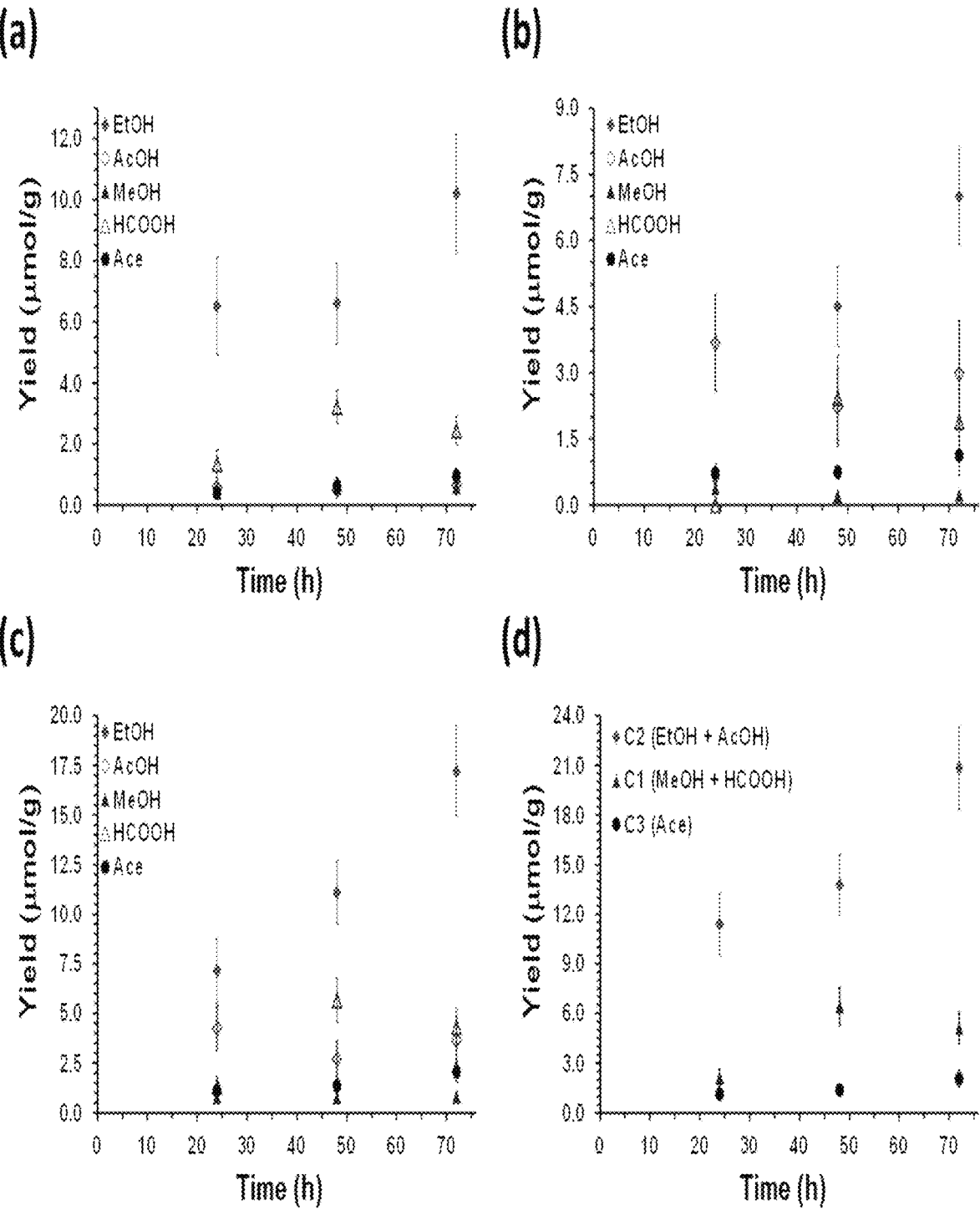
Fig. 14(a)-(d)

PROCESS FOR PRODUCING FUNCTIONALIZED ORGANIC MOLECULES AND USES THEREOF

CROSS-REFERENCE TO RELATED APPLICATIONS

This application is the United States national stage entry of International Application No. PCT/EP2021/060996, filed Apr. 27, 2021, claims priority to European Application No. 20382345.5, filed Apr. 28, 2020, and further claims priority to European Application No. 20382918.9, filed Oct. 21, 2020. The contents of International Application No. PCT/EP2021/060996, European Application No. 20382345.5 and European Application No. 20382918.9 are incorporated by reference herein in their entireties.

FIELD

The present invention relates to a process for producing functionalized organic molecules, in particular having 1 to 3 carbon atoms, and to uses thereof.

BACKGROUND

Carbon dioxide ($CO_2$) is considered the primary greenhouse gas and the main cause for global climate warming. Therefore, the efficient utilization of it as C1 feedstock to synthesize valuable chemical and industrial products is drawing increasing attention. For example, it is known that carbon dioxide may be employed as C1 feedstock to synthesize ethanol (W. Zhang, Y. Hu, L. Ma, G. Zhu, Y. Wang, X. Xue, R. Chen, S. Yang. Z. Jin, Adv. Sci. 2018, 5, 1700275; B. An, Z. Li, Y. Song, J. Z. Zhang, L. Z. Zeng, C. Wang, W. B. Lin, Natur. Catal. 2019, 2, 709-717; C. Liu, B. C. Colón, M. Ciesack, P. A. Silver, D. G. Nocera, Science 2016, 352, 1210-1213; E. S. Wiedner, J. C. Linehan, Chem. Eur. J. 2018, 24, 16964-16971; D. Wang, Q. Y. Bi, G. H. Yin, W. L. Zhao, F. Q. Huang, X. M. Xie, M. H. Jiang, Chem. Commun. 2016, 52, 14226-14229).

Further, it is known that transition metals and complexes that can act as transition metals dominate the catalysis associated to $CO_2$ activation and fixation (C. S. Yeung, Angew. Chem. Int. Ed. 2019, 58, 5492-5502; C. Weetman, S. Inoue, ChemCatChem 2018, 10, 4213-4228; P. P. Power, Nature 2010 463 171-177; D. D. Zhu, J. L. Liu, S. Z. Adv. Mater. 2016, 28, 3423-3452).

Since the carbon atom in $CO_2$ is at the highest oxidation state, the $CO_2$ molecule is very inert and stable. Therefore, the conversion of $CO_2$ into high-value chemicals with one carbon atom (C1; as for example methanol and formic acid), two carbon atoms (C2; as for example ethanol and acetic acid) and three carbon atoms (C3; as for example acetone) requires very efficient electrocatalysts for promoting the kinetically sluggish $CO_2$ reduction process.

Accordingly, there is still further need for processes facilitating the conversion of $CO_2$ into high-value chemicals, in particular as mentioned above.

SUMMARY

In view of the foregoing, the object underlying the present invention is therefore to make available a process for producing, in particular selectively producing, functionalized organic molecules, in particular having 1 to 3 carbon atoms, which addresses the afore-mentioned need.

The present invention relates to a process for producing or synthesizing, in particular selectively producing or synthesizing, functionalized organic molecules, in particular having 1 to 3 carbon atoms, wherein the functionalized organic molecules are preferably selected from the group consisting of ethanol, methanol, formic acid, acetic acid, malonic acid, acetone and a mixture of at least two of the afore-said functionalized organic molecules. Preferably, the present invention relates to a process for producing or synthesizing, in particular selectively producing or synthesizing, ethanol or a mixture comprising or consisting of ethanol and at least one further functionalized organic molecule, preferably selected from the group consisting of methanol, formic acid, acetic acid, malonic acid and acetone, in particular to a mixture comprising or consisting of ethanol, methanol, formic acid, acetic acid and acetone, in particular with ethanol as a major reaction product, or to a mixture comprising or consisting of ethanol, methanol, acetic acid, malonic acid and acetone, in particular with ethanol as a major reaction product.

The process comprises the step of contacting carbon dioxide ($CO_2$) as the only gas, i.e. carbon dioxide and no further gas, in presence of water, in particular liquid water, ($H_2O$) with a catalyst, in particular electrocatalyst, comprising or consisting of permanently polarized hydroxyapatite or contacting a gas mixture comprising or consisting of carbon dioxide ($CO_2$) and methane ($CH_4$), in particular only comprising or consisting of carbon dioxide ($CO_2$) and methane ($CH_4$), in presence of water, in particular liquid water, ($H_2O$) with a catalyst, in particular electrocatalyst, comprising or consisting of permanently polarized hydroxyapatite.

Hereafter, the above step of the inventive process is denoted as "contacting step".

The term "functionalized organic molecules" as used according to the present invention means organic molecules bearing or comprising functional groups, i.e. specific substituents or moieties that are typically responsible for the characteristic chemical reactions of the organic molecules. Preferably, the functional groups are selected from the group consisting of carboxy groups, formyl groups, keto groups, hydroxy groups and combinations thereof.

Further, the term "functionalized organic molecules" as used according to the present invention may refer to one type of organic molecule, for example an alcohol such as ethanol or a carboxylic acid such as formic acid, or to a mixture comprising or consisting of different organic molecules. The different organic molecules, for example, may be different in terms of the number of carbon atoms and/or the functional group.

Preferably, the term "functionalized organic molecules" as used according to the present invention means carboxylic acids, aldehydes, ketones, alcohols or mixtures thereof. More preferably, the carboxylic acids/carboxylic acid are/is formic acid and/or acetic acid and/or malonic acid. The ketones/ketone are/is preferably acetone. The alcohols/alcohol are/is preferably ethanol and/or methanol.

In accordance with the preceding paragraphs, the process according to the present invention is preferably a process for producing or synthesizing, in particular selectively producing or synthesizing, carboxylic acids, in particular different carboxylic acids, having 1 to 3 carbon atoms, preferably formic acid and/or acetic acid, and/or malonic acid, and/or aldehydes, in particular different aldehydes, having 1 to 3 carbon atoms and/or ketones, in particular different ketones, having 1 to 3 carbon atoms, preferably acetone, and/or alcohols, in particular different alcohols, having 1 to 3 carbon atoms, preferably ethanol and/or methanol.

More preferably, the process according to the present invention is a process for producing or synthesizing, in particular selectively producing or synthesizing, functionalized organic molecules which are selected from the group consisting of ethanol, methanol, formic acid, acetic acid, malonic acid, acetone and mixtures thereof, i.e. mixtures of at least two of the afore-said functionalized organic molecules.

Especially preferably, the process according to the present invention is a process for producing or synthesizing, in particular selectively producing or synthesizing, ethanol or a mixture comprising or consisting of ethanol, methanol, formic acid, acetic acid and acetone, in particular with ethanol as a major reaction product, or a mixture comprising or consisting of ethanol, methanol, acetic acid, malonic acid and acetone, in particular with ethanol as a major reaction product.

The term "major reaction product", in particular in the context of ethanol, as used according to the present invention means a product having the highest molar yield within a mixture comprising or consisting of different products, in particular different functionalized organic molecules, in particular having 1 to 3 carbon atoms.

The term "permanently polarized hydroxyapatite" as used according to the present invention means a hydroxyapatite that has undergone a complete structural redistribution, in particular almost perfect, with a high crystallinity degree, i.e. particularly with a low amount of amorphous calcium phosphate and the presence of vacancies detected by increased electrochemical activity and the accumulation of charge per unit mass and surface. It has an electrochemical activity and ionic mobility which do not disappear over time. The corresponding $^{31}$P-NMR spectrum of the permanently polarized hydroxyapatite is as shown on FIG. 1. Preferably, said spectrum is carried out with solid hydroxyapatite using phosphoric acid ($H_3PO_4$) as a reference and showing a unique peak at 2.6 ppm corresponding to phosphate groups of hydroxyapatite.

The term "thermally polarized hydroxyapatite" as used according to the present invention preferably means a permanently polarized hydroxyapatite obtained or obtainable by a process (thermal polarization process) comprising the steps of (a) sintering samples of hydroxyapatite, in particular at a temperature between 700° C. and 1200° C., and (b) applying a constant or variable DC voltage between 250 V and 2500 V, in particular for at least 1 min and/or at a temperature between 900° C. and 1200° C., in particular from 1000° C. to 1200° C., or applying an equivalent field between 1.49 kV/cm and 15 kV/cm, in particular for at least 1 min and/or at a temperature between 900° C. and 1200° C., in particular from 1000° C. to 1200° C., or applying an electrostatic discharge between 2500 V and 1500000 V, in particular for >0 min to 24 h, for example for less than 10 min, and/or at a temperature between 900° C. and 1200° C., in particular from 1000° C. to 1200° C., or applying an equivalent electrical field between 148.9 kV/cm and 8928 kV/cm, in particular for >0 min to 24 h, for example for less than 10 min, and/or at a temperature between 900° C. and 1200° C., in particular from 1000° C. to 1200° C.

The samples of hydroxyapatite in step (a) may be samples of a natural, i.e. naturally occurring, hydroxyapatite or of a synthetic hydroxyapatite.

Further, the samples of hydroxyapatite in step (a) may be in particular selected from the group consisting of samples of crystalline hydroxyapatite, samples of amorphous hydroxyapatite, samples of a mixture of crystalline hydroxyapatite and amorphous calcium phosphate, and mixtures thereof.

Accordingly, the permanently polarized hydroxyapatite of the composition or material according to the present invention is preferably obtained or obtainable by the above process (thermal polarization process).

The term "room temperature" as used according to the present invention means a temperature from 15° C. to 35° C., in particular 18° C. to 30° C., preferably 20° C. to 30° C., more preferably 20° C. to 28° C., particularly 20° C. to 25° C.

The present invention rests on the surprising finding that production or synthesis, in particular selective production or synthesis, of functionalized organic molecules having 1 carbon atom (such as methanol and/or formic acid), functionalized organic molecules having 2 carbon atoms (such as ethanol and/or acetic acid) and functionalized organic molecules having 3 carbon atoms (such as acetone) from carbon dioxide alone or from carbon dioxide and methane in the presence of permanently polarized hydroxyapatite as catalyst is achievable under mild conditions (particularly <10 bar pressure and ≤250° C., in particular <250° C., temperature) with lower levels of environmental contamination and cost. Without wishing to be bound by theory, the production or synthesis of functionalized organic molecules having 1 to 3 carbon atoms according to the present invention involves hydrogenation of reduced carbon dioxide and C—C bond construction. Thus, the process according to the present invention may also be denoted as electro-reduction process of carbon dioxide towards carboxylic acids (such as formic acid and/or acetic acid) and/or aldehydes and/or ketones (such as acetone) and/or alcohols (such as methanol and/or ethanol) and the permanently polarized hydroxyapatite may also be denoted as electro-catalyst.

In an embodiment of the invention, the permanently polarized hydroxyapatite comprises or has a crystallinity >65%, in particular >70%, preferably >75%, more preferably from 65% to 99.9%, and/or a proportion of amorphous calcium phosphate <18% by weight, in particular from 0.1% by weight to 17% by weight or <9% by weight, preferably <5% by weight, in particular <0.1% by weight, based on the total weight of the permanently polarized hydroxyapatite, and/or a proportion of β-tricalcium phosphate <36% by weight, in particular from 0.1% by weight to 35% by weight or <12% by weight, preferably <5% by weight, in particular <0.5% by weight, based on the total weight of the permanently polarized hydroxyapatite, and/or a bulk resistance from $10^7$ Ω cm$^2$ to $10^4$ Ω cm$^2$, in particular $10^7$ Ω cm$^2$ to $10^5$ Ω cm$^2$, in particular $10^6$ Ω cm$^2$ to $10^5$ Ω cm$^2$, preferably of $10^5$ Ω cm$^2$, and/or a surface capacitance which decreases less than 8%, in particular from 8% to 0.1%, preferably from 5% to 3%, after 3 months.

The term "bulk resistance" as used according to the present invention means resistance to the electron transfer and may be determined by means of electrochemical impedance spectroscopy.

Preferably, the bulk resistance increases by only 0.1% to 33%, in particular 4% to 63%, preferably by 4%, after 3 months.

The term "surface capacitance" as used according to the present invention means capacitance attributed to surface changes of hydroxyapatite induced by a thermal polarization process and may be determined by means of electrochemical impedance spectroscopy.

With respect to further features and advantages of the permanently polarized hydroxyapatite as used according to the present invention, it is referred to the PCT application WO 2018/024727 A1, the content of which is incorporated hereby by explicit reference.

In a further embodiment of the invention, the permanently polarized hydroxyapatite is obtained or obtainable by a process comprising the steps of (a) preparing samples of hydroxyapatite, in particular crystalline hydroxyapatite, (b) sintering the samples prepared in step (a), in particular at a temperature between 700° C. and 1200° C., (c) applying a constant or variable DC voltage between 250 V and 2500 V, in particular for at least 1 min and/or at a temperature between 900° C. and 1200° C., in particular from 1000° C. to 1200° C., to the samples obtained in step (b) or to shaped bodies thereof or applying an equivalent electric field between 1.49 kV/cm and 15 kV/cm, in particular for at least 1 min and/or at a temperature between 900° C. and 1200° C., in particular from 1000° C. to 1200° C., to the samples obtained in step (b) or to shaped bodies thereof or applying an electrostatic discharge between 2500 V and 1500000 V, in particular for >0 min to 24 h, for example for less than 10 min, and/or at a temperature between 900° C. and 1200° C., in particular from 1000° C. to 1200° C., to the samples obtained in step (b) or to shaped bodies thereof or applying an equivalent electrical field between 148.9 kV/cm and 8928 kV/cm, in particular for >0 min to 24 h, for example for less than 10 min, and/or at a temperature between 900° C. and 1200° C., in particular from 1000° C. to 1200° C., to the samples obtained in step (b) or to shaped bodies thereof and (d) cooling the samples obtained in step (c) maintaining the DC voltage or the equivalent electric field, or cooling the samples obtained in step (c) maintaining the electrostatic discharge or the equivalent electric field, or cooling the samples obtained in step (c) without maintaining the DC voltage or electrostatic discharge or the equivalent electric field.

The term "samples" as used according to the present invention may in particular mean one sample, i.e. only one sample (singular), or a plurality of samples, i.e. two or more samples. Accordingly, the term "shaped bodies" as used according to the present invention may in particular mean one shaped body, i.e. only one shaped body (singular), or a plurality of shaped bodies, i.e. two or more shaped bodies.

The aforementioned step (a) may be carried out by using ammonium phosphate dibasic (diammonium hydrogen phosphate, $(NH_4)_2HPO_4$) and calcium nitrate $(Ca(NO_3)_2)$ as reactants or starting materials. In particular, the step (a) may be carried out by ($a_1$) providing a mixture, in particular an aqueous mixture, preferably an aqueous-alcoholic mixture, of ammonium phosphate dibasic and calcium nitrate, ($a_2$) stirring the mixture provided in step ($a_1$), in particular at room temperature, ($a_3$) hydrothermal treating of the mixture stirred in step ($a_2$), ($a_4$) cooling the mixture hydrothermally treated in step ($a_3$), ($a_5$) separating precipitates obtained after cooling the mixture in step ($a_4$), and ($a_6$) freeze-drying the precipitates separated in step ($a_5$) to produce hydroxyapatite, in particular crystalline hydroxyapatite.

The step ($a_1$) may be in particular carried out by using a mixture comprising or consisting of ammonium phosphate dibasic, calcium nitrate, water, in particular de-ionized water, ethanol, and optionally chelated calcium solutions. Advantageously, the pH value of the mixture and/or the pH value of an aqueous calcium nitrate solution applied for providing the mixture may be adjusted to 10-12, preferably 10.5. Thus, shapes and sizes of hydroxyapatite, in particular in the form of nanoparticles, can be controlled. Further, the step ($a_2$) may be carried out under agitation, in particular gentle agitation, for example applying 150 rpm to 400 rpm. Further, the step ($a_2$) may be carried out for 1 min to 12 h, in particular for 1 h. The step ($a_2$) may also be termed as an aging step, according to the present invention. Further, the step ($a_3$) may be carried out at a temperature of 60° C. to 240° C., preferably of 150° C. Further, the step ($a_3$) may be carried out at a pressure of 1 bar to 250 bar, preferably of 20 bar. Further, the step ($a_3$) may be carried out for 0.1 h to 72 h, preferably for 24 h. Further, the step ($a_4$) may be carried out by cooling the mixture hydrothermally treated in step ($a_3$) to a temperature of 0° C. to 90° C., in particular of 25° C. Further, the step ($a_5$) may be carried out by means of centrifugation and/or filtration. Further, the precipitates separated in step ($a_5$) may be washed, in particular using water and/or a mixture of ethanol and water, before the step ($a_6$) is carried out. Further, the step ($a_6$) may be carried out for 1 day to 4 days, in particular for 2 days to 3 days, preferably for 3 days.

Further, the aforementioned step (b) may be carried out at a temperature between 700° C. and 1150° C., in particular between 800° C. and 1100° C., in particular at 1000° C.

Further, the process preferably comprises between the step (b) and the step (c) a further step (bc)

pressing the samples obtained in step (b) to form shaped bodies or to form the shaped bodies thereof, i.e. to form the shaped bodies of the samples obtained in step (b).

In particular, the step (bc) may be carried out under a pressure of 1 MPa to 1000 MPa, in particular 100 MPa to 800 MPa, preferably 600 MPa to 700 MPa. Further, the step (bc) may be carried out for 1 min to 90 min, in particular 5 min to 50 min, preferably 10 min to 30 min.

The shaped bodies may have a polygonal, for example triangular, quadratic or rectangular, pentagonal, hexagonal, heptagonal, octagonal or nonagonal, or a corner-less, in particular circular, oval-shaped or elliptical, cross-section. Further, the shaped bodies may have a thickness of >0 cm to 10 cm, in particular >0 cm to 5 cm, preferably >0 cm to 2 cm. In particular, the shaped bodies may have a thickness of 0.1 cm to 10 cm in particular 0.1 cm to 5 cm, preferably 0.5 cm to 2 cm.

Preferably, the shaped bodies are in the form of discs, plates, cones or cylinders.

Advantageously, by carrying out step (c), catalytic activation of the samples obtained in step (b) or the shaped bodies thereof may be accomplished. Preferably, step (c) is carried out by placing the samples obtained in step (b) or by placing the shaped bodies thereof between a positive electrode and a negative electrode, wherein the samples obtained in step (b) or the shaped bodies thereof are in contact with both electrodes. The electrodes may, by way of example, be in the form of stainless steel plates, in particular stainless steel AISI 304 plates. Further, the electrodes may have a mutual distance of 0.01 mm to 10 cm, in particular 0.01 mm to 5 cm, preferably 0.01 mm to 1 mm.

The electrodes can be of different shapes. The electrodes may have a polygonal cross-section, for example quadratic or rectangular, or a corner-less, in particular circular, oval-shaped or elliptical, cross-section. In particular, the electrodes may have a thickness of >0 cm to 10 cm in particular >0 cm to 5 cm, preferably >0 cm to 1 mm. For example, the electrodes may be in the form of a disc, plate or a cylinder.

Further, the constant or variable DC voltage or the equivalent electric field may be applied in the aforementioned step (c) for 1 h to 24 h, in particular 0.1 h to 10 h, in particular 1 h.

Further, the DC voltage applied in the aforementioned step (c) is preferably 500 V, which is equivalent to a constant electric field of 3 kV/cm.

Further, the equivalent electric field applied in the aforementioned step (c) is preferably 3 kV/cm.

Further, the temperature in the aforementioned step (c) is preferably at least 900° C., more preferably at least 1000° C. Preferably, the temperature in step (c) is 900° C. to 1200° C., in particular 1000° C. to 1200° C., particularly 1000° C.

Preferably, step (c) is carried out by applying a constant or variable DC voltage of 500 V at 1000° C. for 1 h to the samples obtained in step (b) or the shaped bodies, in particular discoidal shaped bodies, thereof.

Further, the aforementioned step (d) may be carried out by cooling the samples obtained in step (c) to room temperature.

Further, the aforementioned step (d) may be carried out for 1 min to 72 h, in particular 15 min to 5 h, preferably 15 min to 2 h.

In a further embodiment of the invention, the permanently polarized hydroxyapatite is obtained or obtainable by a process comprising the steps of (a) preparing samples of hydroxyapatite, in particular crystalline hydroxyapatite, in particular using ammonium phosphate dibasic (diammonium hydrogen phosphate, $(NH_4)_2HPO_4$) and calcium nitrate $(Ca(NO_3)_2)$ as reactants or starting materials, (b) sintering the samples prepared in step (a), in particular at a temperature of 1000° C., in particular for 2 h, (c) applying an equivalent electric field of 3 kV/cm, in particular at a temperature of 1000° C., in particular for 1 h, to the samples obtained in step (b) or to shaped bodies thereof and (d) cooling the samples obtained in step (c) maintaining the equivalent electric field, in particular for 30 min.

With respect to further features and advantages of the steps (a)-(d), reference is made in its entirety to the previous description.

In a further embodiment of the invention, the contacting step is carried out in the presence of liquid water and/or water vapor. In other words, according to a further embodiment of the invention, the water is in liquid form and/or vapor form, for carrying out the contacting step.

In a further embodiment of the invention, the contacting step is carried out with a volumetric ratio of permanently polarized hydroxyapatite to water, in particular liquid water and/or water vapor, of 1000:1 to 0.01:1, in particular 500:1 to 100:1, preferably 300:1 to 350:1.

In a further embodiment of the invention, the contacting step is carried out with carbon dioxide alone.

In a further embodiment of the invention, the contacting step is carried out with a volumetric ratio of carbon dioxide to methane of 200:1, in particular 3:1, preferably 1:1.

In a further embodiment of the invention, the contacting step is carried out under a total pressure of 0.1 bar to 100 bar, in particular 0.1 bar to 10 bar, in particular 1 bar to 10 bar, in particular 1 bar to 8 bar, in particular 1 bar to 6 bar, preferably of 6 bar.

The term "total pressure" as used according to the present invention refers to the carbon dioxide pressure (when this gas is used alone) or to the sum of each gas partial pressure of the gas mixture, preferably at room temperature.

In a further embodiment of the invention, the contacting step is carried out under a pressure of carbon dioxide of 0.035 bar to 90 bar, in particular 0.1 bar to 10 bar, in particular 1 bar to 8 bar, preferably of 6 bar.

In a further embodiment of the invention, the contacting step is carried out under a partial pressure of carbon dioxide of 0.035 bar to 90 bar, in particular 0.1 bar to 3 bar, in particular 1 bar to 3 bar, preferably of 3 bar, and/or under a partial pressure of methane of 0.00017 bar to 5 bar, in particular 1 bar to 3 bar, preferably of 3 bar.

Further, the contacting step may be carried out with a total pressure of the gas mixture from 0.0001 bar to 250 bar in the presence of the catalyst and the water, in particular liquid water.

Further, the contacting step may be carried out with a pressure ratio of carbon dioxide to methane $(CO_2:CH_4)$ in the presence of the catalyst from 0.0001 bar:250 bar to 250 bar:0.0001 bar.

Further, the gas mixture may be in particular free of nitrogen $(N_2)$. In other words, the contacting step may be carried out in the absence of nitrogen.

In a further embodiment of the invention, the contacting step is carried out with a molar ratio of carbon dioxide to permanently polarized hydroxyapatite of 0.1 to 0.5, in particular 0.2 to 0.5, preferably 0.3 to 0.5.

In a further embodiment of the invention, the contacting step is carried out with a molar ratio of methane to permanently polarized hydroxyapatite of 0.1 to 0.5, in particular 0.2 to 0.5, preferably 0.3 to 0.5.

Preferably, the contacting step is carried out by using an uncoated permanently polarized hydroxyapatite, i.e. by using a permanently polarized hydroxyapatite lacking any coating. In that regard, it surprisingly turned out that the application of an uncoated permanently polarized hydroxyapatite advantageously significantly increases the conversion of carbon dioxide into functionalized organic molecules having 2 and/or 3 carbon atoms (such as ethanol and/or acetic acid and/or acetone) and particularly in addition maximizes the selective synthesis of ethanol as the major reaction product. Similarly, the application of an uncoated permanently polarized hydroxyapatite advantageously significantly increases the conversion of carbon dioxide and methane into ethanol and particularly in addition maximizes the selective synthesis of ethanol as the major reaction product.

Alternatively, the contacting step may be carried out by using a coated permanently polarized hydroxyapatite. In principle, the contacting step may be carried out by using a permanently polarized hydroxyapatite being coated with an inorganic photocatalyst such as $TiO_2$, $MgO_2$, $MnO_2$ or combinations thereof. More specifically, the contacting step may be carried out by using a permanently polarized hydroxyapatite having a three-layered coating, in particular wherein the three-layered coating may be composed of two layers of aminotris(methylenephosphonic acid) and a layer of zirconium oxychloride ($ZrOCl_2$) or zirconia ZrO2, wherein the layer of zirconium oxychloride is arranged or sandwiched between the two layers of aminotris(methylene-phosphonic acid). By using a coated permanently polarized hydroxyapatite, the efficiency of the reaction can be advantageously increased.

In a further embodiment of the invention, the contacting step is carried out under UV (ultraviolet) irradiation or UV-Vis (ultraviolet-visible) irradiation. In particular, the contacting step may be carried out under UV irradiation or UV-Vis irradiation having a wavelength from 200 nm to 850 nm, in particular 240 nm to 400 nm, preferably 250 nm to 260 nm, more preferably of 253.7 nm. Further, the contacting step may be in particular carried out under UV irradiation having a wavelength from 200 nm to 280 nm, in particular 240 nm to 270 nm, preferably 250 nm to 260 nm, more preferably of 253.7 nm. Preferably, the permanently polarized hydroxyapatite is directly exposed to or irradiated with the UV irradiation or UV-Vis irradiation. Advantageously, the UV irradiation or UV-Vis irradiation are/is provided by a suitable UV source and/or Vis source, for example UV lamp and/or Vis lamp.

In a further embodiment of the invention, the contacting step is carried out under UV (ultraviolet) irradiation or UV-Vis (ultraviolet-visible) irradiation having a irradiance from 0.1 $W/m^2$ to 200 $W/m^2$, in particular 1 $W/m^2$ to 50 $W/m^2$, preferably 2 $W/m^2$ to 10 $W/m^2$, more preferably of 3 $W/m^2$. With respect to advantages of this embodiment, reference is made to the preceding paragraph.

In a further embodiment of the invention, the contacting step is carried out at a temperature of 25° C. to 250° C., in particular 95° C. to 140° C., preferably of 95° C.

More preferably, the contacting step is carried out at a temperature of 95° C. and under UV irradiation. These reaction conditions are especially useful for synthesizing, in particular selectively synthesizing, functionalized organic molecules having 2 carbon atoms (such as ethanol and/or acetic acid) in high yields.

Further, the contacting step may be preferably carried out without UV irradiation and at a temperature of 25° C. to 250° C., in particular 95° C. to 140° C., preferably of 140° C. Also, the reaction conditions according this embodiment result in the synthesis, in particular selective synthesis, of functionalized organic molecules having 2 carbon atoms (such as ethanol and/or acetic acid) in high yields.

Further, the contacting step may be carried out for 0.0001 h to 120 h, in particular 24 h to 72 h, preferably 48 h to 72 h.

Further, the process, in particular the contacting step, may be carried out continuously or discontinuously, in particular as a batch process.

Further, the contacting step may be carried out by using air, in particular traffic contaminated air, as gas mixture. Thus, it is possible to synthesize functionalized organic molecules having 1 to 3 carbon atoms, in particular ethanol and/or acetic acid and/or methanol and/or formic acid and/or acetone, as valuable compounds and concurrently to remove carbon dioxide from air, in particular traffic contaminated air.

Preferably, the process comprises a further step isolating and/or separating and/or purifying the functionalized organic molecules obtained during or in the contacting step.

The above further step is preferably carried out by dissolving and extracting the catalyst and/or by extracting a supernatant formed during or in the contacting step.

In a further embodiment of the invention, the process is used for producing or synthesizing, in particular selectively producing or synthesizing, ethanol.

In a further embodiment of the invention, the process is used for producing or synthesizing a mixture comprising or consisting of ethanol and at last one further functionalized organic molecule, preferably selected from the group consisting of methanol, formic acid, acetic acid, malonic acid and acetone.

More preferably, the process is used for producing or synthesizing a mixture comprising or consisting of ethanol and at last one further functionalized organic molecule selected from the group consisting of methanol, formic acid, acetic acid and acetone.

Alternatively, the process is preferably used for producing or synthesizing a mixture comprising or consisting of ethanol and at last one further functionalized organic molecule selected from the group consisting of methanol, acetic acid, malonic acid and acetone.

In a further embodiment of the invention, the process is used for producing or synthesizing a mixture comprising or consisting of ethanol, methanol, formic acid, acetic acid and acetone.

In a further embodiment of the invention, the process is used for producing or synthesizing a mixture comprising or consisting of ethanol, methanol, acetic acid, malonic acid and acetone.

Further, the present invention relates to the use of the process according to the present invention for removing carbon dioxide from an atmosphere, in particular from air, i.e. atmosphere of Earth. In particular, the present invention relates to the use of the process according to the present invention for removing carbon dioxide from polluted or contaminated air such as traffic contaminated air.

The term "air" or "atmosphere of Earth" as used according to the present invention means a layer of gases retained by Earth's gravity, surrounding the planet's Earth and forming its planetary atmosphere.

With respect to further features and advantages of the use, reference is made in its entirety to the previous description.

Finally, the present invention relates to the use of a process comprising the step of contacting carbon dioxide ($CO_2$) as the only gas, i.e. carbon dioxide and no further gas, in presence of water, in particular liquid water, ($H_2O$) with a catalyst, in particular electrocatalyst, comprising or consisting of permanently polarized hydroxyapatite or contacting a gas mixture comprising or consisting of carbon dioxide ($CO_2$) and methane ($CH_4$), in particular only comprising or consisting of carbon dioxide ($CO_2$) and methane ($CH_4$), in presence of water, in particular liquid water, ($H_2O$) with a catalyst, in particular electrocatalyst, comprising or consisting of permanently polarized hydroxyapatite for the production or synthesis, in particular selective production or synthesis, of organic molecules, in particular having 1 to 3 carbon atoms, wherein the functionalized organic molecules are preferably selected from the group consisting of ethanol, methanol, formic acid, acetic acid, malonic acid, acetone and a mixture of at least two of the afore-said functionalized organic molecules.

Preferably, said use of the process is for the production or synthesis, in particular selective production or synthesis, of ethanol or a mixture comprising or consisting of ethanol and at least one further functionalized organic molecule selected from the group consisting of methanol, formic acid, acetic acid, malonic acid and acetone, in particular to a mixture comprising or consisting of ethanol, methanol, formic acid, acetic acid and acetone, in particular with ethanol as a major reaction product, or to a mixture comprising or consisting of ethanol, methanol, acetic acid, malonic acid and acetone, in particular with ethanol as a major reaction product. With respect to further features and advantages of the use, in particular in terms of the process and the functionalized organic molecules, reference is made in its entirety to the previous description.

Further features and advantages of the invention will become clear from the following examples. The individual features can be realized either singularly or severally in combination in one embodiment of the invention. The preferred embodiments merely serve for illustration and better understanding of the invention and are not to be understood as in any way limiting the invention.

BRIEF DESCRIPTION OF THE DRAWINGS

For a better understanding of what has been disclosed, some figures are attached which schematically or graphically and solely by way of non-limiting example show a practical case of embodiment of the present invention.

FIG. 2($b$) schematically depicts the Raman spectra of permanently polarized hydroxyapatite (p-HAp) samples with the deconvolution of the $v_1$ peak in the 930-990 cm$^{-1}$ interval.

FIG. 3($a$) shows a scanning electron microscopy micrograph of the permanently polarized hydroxyapatite.

FIG. 3($b$) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) in the presence of conventional (i.e. non-polarized) hydroxyapatite as a catalyst, at 95° C. under UV radiation.

FIG. 3($c$) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) using (uncoated) permanently polarized hydroxyapatite as catalyst, at 95° C. under UV radiation.

FIG. 3($d$) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) in the presence of coated p-HAp. The p-HAp was coated with aminotris(methylenephosphonic acid), hereafter denoted as ATMP, and zirconium oxychloride (ZrOCl$_2$), hereafter denoted as ZC, at 95° C. under UV radiation.

FIG. 4($a$) graphically shows a further $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions.

FIG. 4($b$) graphically shows the $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. without UV radiation as reaction conditions.

FIG. 4($c$) graphically shows the $^1$H-NMR spectrum of a solution obtained after extraction of the reaction products achieved after 72 h from $CO_2$ (3 bar), $CH_4$ (3 bar) and $H_2O$ (1 mL) using permanently polarized hydroxyapatite as catalyst and 140° C. without UV radiation as reaction conditions.

FIG. 4($d$) graphically shows a further $^1$H-NMR spectrum of the liquid water after reaction for 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions. Spectra were cut to avoid the very intense peak of water at 4.7 ppm.

FIG. 4($e$) graphically shows a further $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions.

FIG. 8($b$) graphically shows the $^1$H-NMR spectra of the reaction products achieved after 72 h from $CO_2$ (3 bar), $CH_4$ (3 bar) and $H_2O$ (1 mL) at 95° C. using UV radiation and using (uncoated) permanently polarized hydroxyapatite as catalyst, wherein liquid water, which has been incorporated to the reaction chamber, has been analyzed.

FIG. 9($b$) graphically shows the $^1$H-NMR spectrum of the reaction products achieved after 72 h from $CO_2$ (3 bar) and $CH_4$ (3 bar) at 95° C. using UV radiation and (uncoated) permanently polarized hydroxyapatite as catalyst with an excess of water.

FIG. 10 graphically shows the $^1$H-NMR spectrum of the solution obtained after extraction of the reaction products achieved after 72 h from polluted air (atmospheric pressure)

Figure 1:
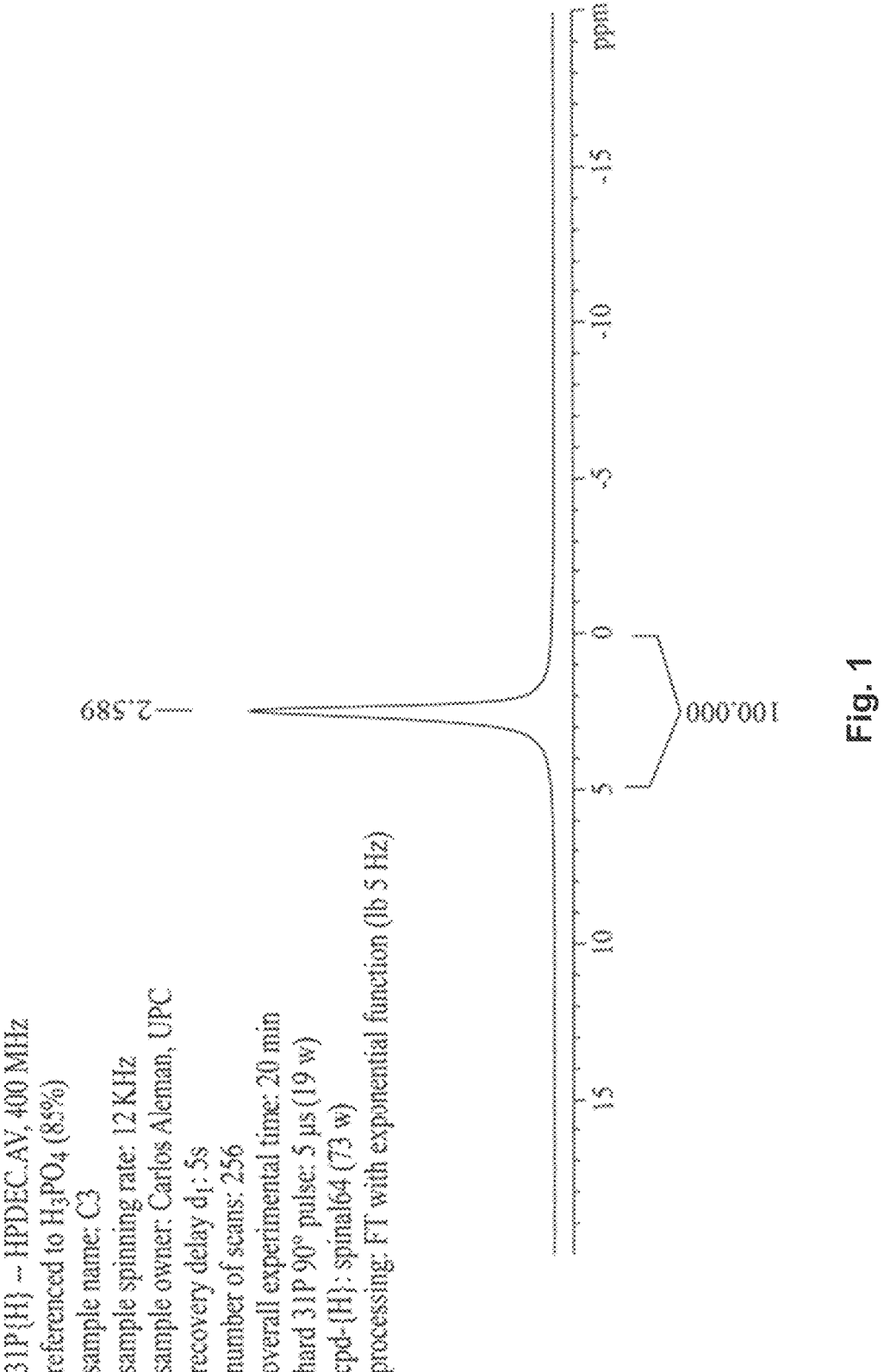
FIG. 1 graphically shows a $^{31}$P-NMR spectrum of the permanently polarized hydroxyapatite (p-HAp) according to the present invention.

and $H_2O$ (1 mL) at 95° C. using (uncoated) permanently polarized hydroxyapatite as catalyst at 95° C. and under UV radiation.

FIG. 11(*a*) graphically shows a further $^1$H-NMR spectrum of the liquid water after reaction for 48 h from $CO_2$ (6 bar) and $H_2O$ (1 mL) using (uncoated) permanently polarized hydroxyapatite as catalyst and 140° C. as reaction conditions (without UV radiation).

FIG. 11(*b*) graphically shows a further $^1$H-NMR spectrum of a solution obtained after extraction of the reaction products achieved after 48 h from $CO_2$ (6 bar) and $H_2O$ (1 mL) using (uncoated) permanently polarized hydroxyapatite as catalyst and 140° C. as reaction conditions (without UV radiation).

FIG. 12(*a*) graphically shows the variation of the yield (expressed as µmol of product/g of catalyst) of ethanol (EtOH), acetic acid (AcOH), methanol (MeOH), formic acid (HCOOH) and acetone (Ace) against the $CO_2$ pressure (in bars) as determined by $^1$H NMR spectroscopy from the solution obtained after extraction of the reaction products achieved after 48 h using $CO_2$ (1, 2, 4 or 6 bars) and $H_2O$ (1 mL) at 140° C. (without UV radiation).

FIG. 12(*b*) graphically shows the variation of the yield (expressed as µmol of product/g of catalyst) of ethanol (EtOH), acetic acid (AcOH), methanol (MeOH), formic acid (HCOOH) and acetone (Ace) against the $CO_2$ pressure (in bars) as determined by $^1$H NMR spectroscopy from the liquid water using (uncoated) permanently polarized hydroxyapatite as catalyst.

FIG. 12(*c*) graphically shows the variation of the sum of the yields (expressed as µmol of product/g of catalyst) achieved from the solution obtained after extraction of the reaction products from the catalyst (FIG. 12*a*) and the supernatant (FIG. 12*b*) for ethanol (EtOH), acetic acid (AcOH), methanol (MeOH), formic acid (HCOOH) and acetone (Ace) against the $CO_2$ pressure (in bars).

FIG. 12(*d*) graphically shows the variation of the sum of the yields (expressed as µmol of product/g of catalyst) achieved from the solution obtained after extraction of the reaction products from the catalyst (FIG. 12*a*) and supernatant (FIG. 12*b*) for C1 (methanol and formic acid; MeOH+HCOOH), C2 (ethanol and acetic acid; EtOH+AcOH) and C3 (acetone; Ace) against the $CO_2$ pressure (in bars).

FIG. 13(*a*) graphically shows the variation of the yield (expressed as µmol of product/g of catalyst) of ethanol (EtOH), acetic acid (AcOH), methanol (MeOH), formic acid (HCOOH) and acetone (Ace) against the temperature (in ° C.) as determined by $^1$H NMR spectroscopy from the solution obtained after extraction of the reaction products achieved after 48 h using $CO_2$ (6 bars) and $H_2O$ (1 mL) at 95, 120 or 140° C. (without UV radiation).

FIG. 13(*b*) graphically shows the variation of the yield (expressed as µmol of product/g of catalyst) of ethanol (EtOH), acetic acid (AcOH), methanol (MeOH), formic acid (HCOOH) and acetone (Ace) against the temperature (in ° C.) as determined by $^1$H NMR spectroscopy from the liquid water using (uncoated) permanently polarized hydroxyapatite as catalyst.

FIG. 13(*c*) graphically shows the variation of the sum of the yields (expressed as µmol of product/g of catalyst) achieved from the solution obtained after extraction of the reaction products from the catalyst (FIG. 13*a*) and the supernatant (FIG. 13*b*) for ethanol (EtOH), acetic acid (AcOH), methanol (MeOH), formic acid (HCOOH) and acetone (Ace) against the temperature (in ° C.).

FIG. 13(*d*) graphically shows the variation of the sum of the yields (expressed as µmol of product/g of catalyst)

achieved from the solution obtained after extraction of the reaction products from the catalyst (FIG. 13*a*) and supernatant (FIG. 13*b*) for C1 (methanol and formic acid; MeOH+HCOOH), C2 (ethanol and acetic acid; EtOH+AcOH) and C3 (acetone; Ace) against the temperature (in ° C.). In all cases the reaction was conducted for 48 h using $CO_2$ (6 bars) and $H_2O$ (1 mL) at 95, 120 or 140° C. (without UV radiation).

FIG. 14(*a*) graphically shows the variation of the yield (expressed as µmol of product/g of catalyst) of ethanol (EtOH), acetic acid (AcOH), methanol (MeOH), formic acid (HCOOH) and acetone (Ace) against the reaction time (in hours) as determined by $^1$H NMR spectroscopy from the solution obtained after extraction of the reaction products achieved after 24, 48 and 72 h using $CO_2$ (6 bars) and $H_2O$ (1 mL) at 140° C. (without UV radiation).

FIG. 14(*b*) graphically shows the variation of the yield (expressed as µmol of product/g of catalyst) of ethanol (EtOH), acetic acid (AcOH), methanol (MeOH), formic acid (HCOOH) and acetone (Ace) against the time (in hours) as determined by $^1$H NMR spectroscopy from the liquid water using (uncoated) permanently polarized hydroxyapatite as catalyst.

FIG. 14(*c*) graphically shows the variation of the sum of the yields (expressed as mol of product/g of catalyst) achieved from the solution obtained after extraction of the reaction products from the catalyst (FIG. 14*a*) and the supernatant (FIG. 14*b*) for ethanol (EtOH), acetic acid (AcOH), methanol (MeOH), formic acid (HCOOH) and acetone (Ace) against the time (in hours).

FIG. 14(*d*) graphically shows the variation of the sum of the yields (expressed as mol of product/g of catalyst) achieved from the solution obtained after extraction of the reaction products from the catalyst (FIG. 14*a*) and supernatant (FIG. 14*b*) for C1 (methanol and formic acid; MeOH+HCOOH), C2 (ethanol and acetic acid; EtOH+AcOH) and C3 (acetone; Ace) against the time (in hours).

Figure 15:
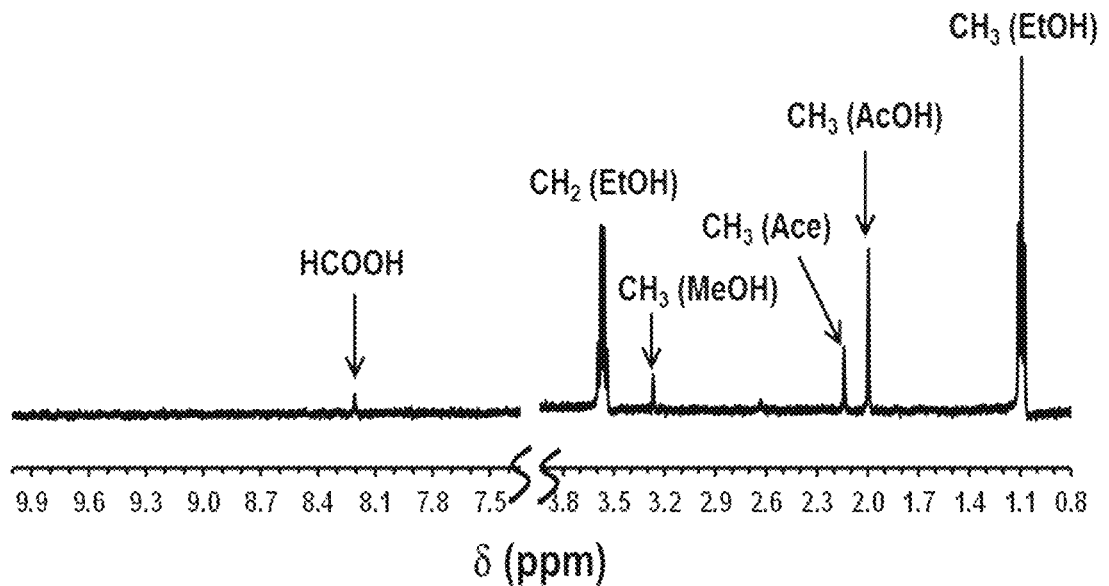

FIG. 15 graphically shows the $^1$H-NMR spectrum of the solution obtained after extraction of the reaction products achieved after 72 h from polluted air (atmospheric pressure) and $H_2O$ (1 mL) at 95° C. using (uncoated) permanently polarized hydroxyapatite as catalyst at 95° C. and under UV radiation.

DETAILED DESCRIPTION

FIG. 1 graphically shows a $^{31}$P-NMR spectrum of the permanently polarized hydroxyapatite (p-HAp) according to the present invention.

Figures 2A, 2B:
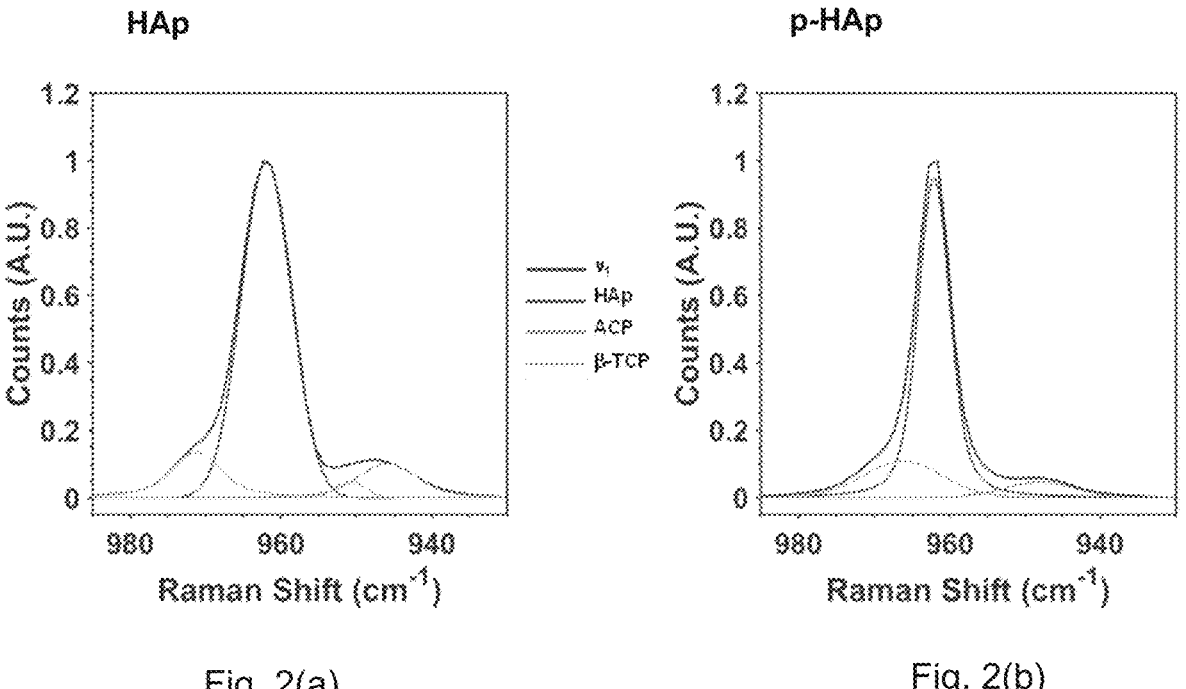
FIG. 2($a$) schematically depicts the Raman spectra of hydroxyapatite (HAp) samples with the deconvolution of the $v_1$ peak in the 930-990 cm$^{-1}$ interval.

FIG. 2(*a*) schematically depicts the Raman spectra of hydroxyapatite (HAp) samples with the deconvolution of the $v_1$ peak in the 930-990 cm$^{-1}$ interval. Counts (A.U.) are plotted on the ordinate. Raman shift (cm$^{-1}$) is plotted on the abscissa.

FIG. 2(*b*) schematically depicts the Raman spectra of permanently polarized hydroxyapatite (p-HAp) samples with the deconvolution of the $v_1$ peak in the 930-990 cm$^{-1}$ interval. Counts (A.U.) are plotted on the ordinate. Raman shift (cm$^{-1}$) is plotted on the abscissa.

FIGS. 2(*a*) and 2(*b*), which compare the Raman $v_1$ peak in the 930-990 cm$^{-1}$ interval before and after polarization of Hap, prove the success of the polarization process.

The area of HAp, amorphous calcium phosphate (ACP) and β-tricalcium phosphate (β-TCP) indicates the content of each phase. The content of co-existing phases experiences a reduction in polarized samples (i.e. 4.3% and 9.8% for ACP and β-TCP, respectively) that is accompanied by a decrease of the full width at half maximum (FWHM) from 9 cm$^{-1}$ in HAp to 5 cm$^{-1}$ in p-HAp. This result indicates an increase of the HAp phase by means of a reduction of crystal imperfections, such as $PO_4^{3-}$ tetrahedrons distortions.

FIG. 3(*a*) shows a scanning electron microscopy micrograph of the permanently polarized hydroxyapatite. Accordingly, the permanently polarized hydroxyapatite can be described as particles of (approximately) 100 nm to 300 nm that aggregate forming agglomerates of up to 1 μm in size.

FIG. 3(*b*) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) in the presence of conventional (i.e. non-polarized) hydroxyapatite as a catalyst, at 95° C. under UV radiation. The reacted catalyst was dissolved in an aqueous solution with 100 mM HCl and 50 mM NaCl.

FIG. 3(*c*) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) using (uncoated) permanently polarized hydroxyapatite as catalyst, at 95° C. under UV radiation. The reacted catalyst was dissolved in an aqueous solution with 100 mM HCl and 50 mM NaCl.

FIG. 3(*d*) graphically shows the $^1$H-NMR spectrum of a solution obtained after extraction of the reaction products of a reaction that was conducted for 72 h using $CO_2$ (3 bar), $CH_4$ (3 bar), $H_2O$ (1 mL) in the presence of coated p-HAp. The p-HAp was coated with aminotris(methylenephosphonic acid), hereafter denoted as ATMP, and zirconium oxychloride ($ZrOCl_2$), hereafter denoted as ZC, at 95° C. under UV radiation. The reacted catalyst was dissolved in an aqueous solution with 100 mM HCl and 50 mM NaCl.

As is shown in FIGS. 3(*b*)-(*d*), chemical shifts observed after the dissolution of the coated p-HAp are slightly deshielded with respect to the peaks of products derived from non-coated catalysts. This effect has been attributed to the aminotris(methylenephosphonic acid) (ATMP), which increases the acidity of the medium, causing downfield shifts that are not detected for p-HAp and HAp, independently of the conditions. On the other hand, FIGS. 3(*b*) and 3(*c*) indicate that the elimination of the coating from the catalyst not only increases the conversion into ethanol by 20%, but also maximizes the selective synthesis of ethanol as the major reaction product.

FIG. 4(*a*) graphically shows a further $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions. The catalyst was dissolved in an aqueous solution with 100 mM HCl and 50 mM NaCl.

FIG. 4(*b*) graphically shows the $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. without UV radiation as reaction conditions. The catalyst was dissolved in an aqueous solution with 100 mM HCl and 50 mM NaCl.

FIG. 4(*c*) graphically shows the $^1$H-NMR spectrum of a solution obtained after extraction of the reaction products achieved after 72 h from $CO_2$ (3 bar), $CH_4$ (3 bar) and $H_2O$ (1 mL) using permanently polarized hydroxyapatite as catalyst and 140° C. without UV radiation as reaction conditions. The catalyst was dissolved in an aqueous solution with 100 mM HCl and 50 mM NaCl.

FIG. 4(*d*) graphically shows a further $^1$H-NMR spectrum of the liquid water after reaction for 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions. Spectra were cut to avoid the very intense peak of water at 4.7 ppm.

FIG. 4(*e*) graphically shows a further $^1$H-NMR spectrum of a solution obtained after extraction of the reaction products achieved after 72 h from $CO_2$ (3 bar), $CH_4$ (3 bar) and $H_2O$ (1 mL) using (uncoated) permanently polarized hydroxyapatite as catalyst and 95° C. and UV radiation as reaction conditions. The catalyst was dissolved in an aqueous solution with 100 mM HCl and 50 mM NaCl. Spectra were cut to avoid the very intense peak of water at 4.7 ppm.

The spectra reveal the apparition of methanol and formic acid as reaction products in the liquid water used for the reaction. Ethanol and acetic acid appears in both the catalyst and the liquid water, while acetone is only detected in the former.

Figure 5:
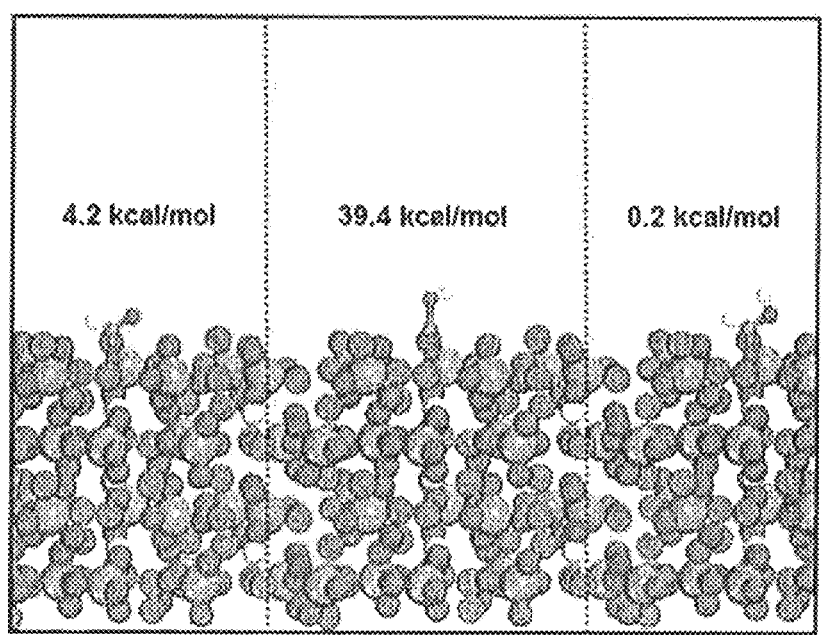
FIG. 5 graphically shows representation of three protonated forms of $CO_2$ adsorbed molecules on the OH$^-$ vacancy of permanently polarized hydroxyapatite.

FIG. 5 graphically shows representation of three protonated forms of $CO_2$ adsorbed molecules on the OH$^-$ vacancy of permanently polarized hydroxyapatite. The numeric values (in eV) stand for the calculated adsorption energies.

In order to support the p-HAp fixation mechanism based on the formation of carboxylates, DFT calculations were performed at the PBE-D3 level. Calculations were performed considering the (0001) facet, which is the most stable HAp surface, and considering an isodesmic model in which $H_2$ is used as a source of protons. The adsorption energies of three different protonation products of $CO_2$ were calculated by inserting the molecules in the hydroxyl vacancy of the mineral. Results proved that the protonation of $CO_2$ to formic acid is exothermic in the gas phase by −3.1 kcal/mol, but it is more exothermic when adsorbed on p-HAp substrate, by −32.7 kcal/mol. Yet, all protonated species display endothermic adsorption energies, the one for the protonated formic acid is very small (0.2 kcal/mol) while the one for the $CO_2$ is 5.1 kcal/mol (other sites were checked on the p-HAp displaying higher energies, as shown for some representative cases in FIG. 5), thus making this pathway unfeasible to be followed completely and shifting the catalysis location elsewhere close to.

Figure 6:
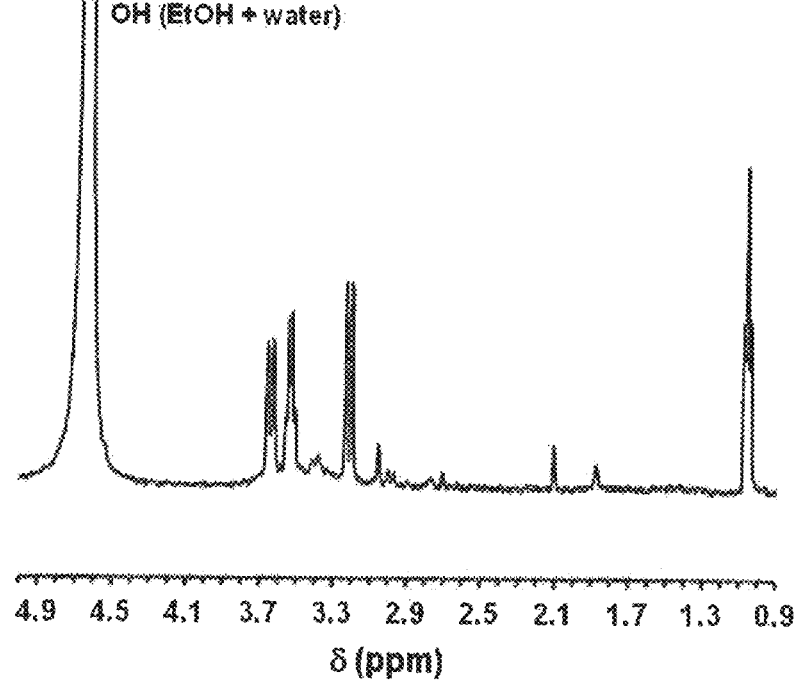
FIG. 6 graphically shows a further $^1$H-NMR spectrum of a solution obtained after extraction of the reaction products achieved after 72 h from $CO_2$ (3 bar), $CH_4$ (3 bar) and $H_2O$ (1 mL) in the presence of permanently polarized hydroxyapatite coated with aminotris(methylenephosphonic acid) and zirconium oxychloride, at 95° C. under UV radiation.

FIG. 6 graphically shows a further $^1$H-NMR spectrum of a solution obtained after extraction of the reaction products achieved after 72 h from $CO_2$ (3 bar), $CH_4$ (3 bar) and $H_2O$ (1 mL) in the presence of permanently polarized hydroxyapatite coated with aminotris(methylenephosphonic acid) and zirconium oxychloride, at 95° C. under UV radiation. The reacted catalyst was dissolved in an aqueous solution with 100 mM HCl and 50 mM NaCl. The spectrum includes the OH band at 4.65 ppm.

Figure 7:
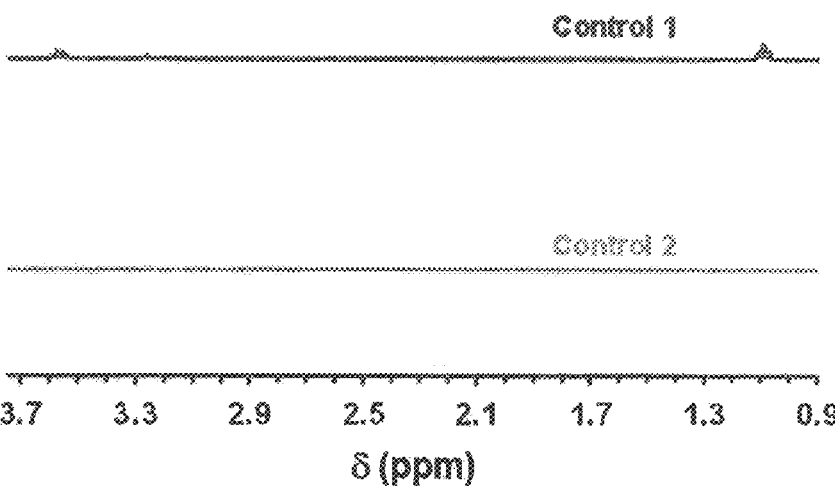
FIG. 7 graphically shows the $^1$H-NMR spectrum of the liquid water after 72 h from $CO_2$ (3 bar), $CH_4$ (3 bar) and $H_2O$ (1 mL) at 95° C. using UV radiation (control 1) and without using UV radiation (control 2).

FIG. 7 graphically shows the $^1$H-NMR spectrum of the liquid water after 72 h from $CO_2$ (3 bar), $CH_4$ (3 bar) and $H_2O$ (1 mL) at 95° C. using UV radiation (control 1) and without using UV radiation (control 2). No catalyst was used for this reaction.

Figure 8:
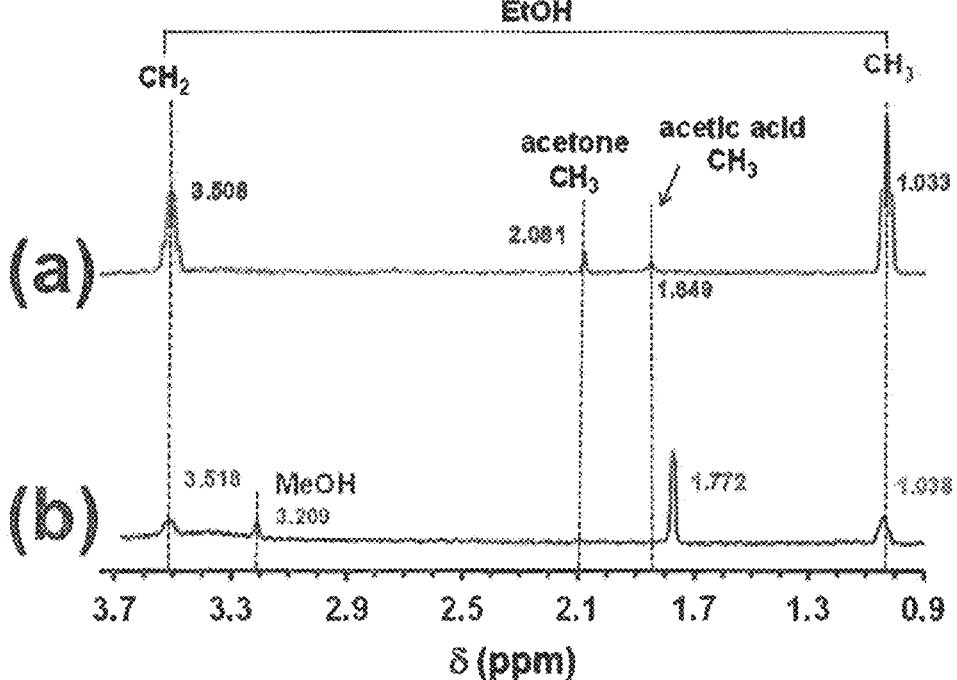
FIG. 8($a$) shows a further $^1$H-NMR spectrum of the reaction products achieved after 72 h from $CO_2$ (3 bar), $CH_4$ (3 bar) and $H_2O$ (1 mL) at 95° C. using UV radiation and (uncoated) permanently polarized hydroxyapatite as catalyst, wherein the analysis of the solution obtained after extraction of the products was performed by dissolving the catalyst with 100 mM HCl and 50 mM NaCl.

FIG. 8(*a*) shows a further $^1$H-NMR spectrum of the reaction products achieved after 72 h from $CO_2$ (3 bar), $CH_4$ (3 bar) and $H_2O$ (1 mL) at 95° C. using UV radiation and (uncoated) permanently polarized hydroxyapatite as catalyst, wherein the analysis of the solution obtained after extraction of the products was performed by dissolving the catalyst with 100 mM HCl and 50 mM NaCl.

FIG. 8(*b*) graphically shows the $^1$H-NMR spectra of the reaction products achieved after 72 h from $CO_2$ (3 bar), $CH_4$ (3 bar) and $H_2O$ (1 mL) at 95° C. using UV radiation and using (uncoated) permanently polarized hydroxyapatite as catalyst, wherein liquid water, which has been incorporated to the reaction chamber, has been analyzed.

Figure 9:
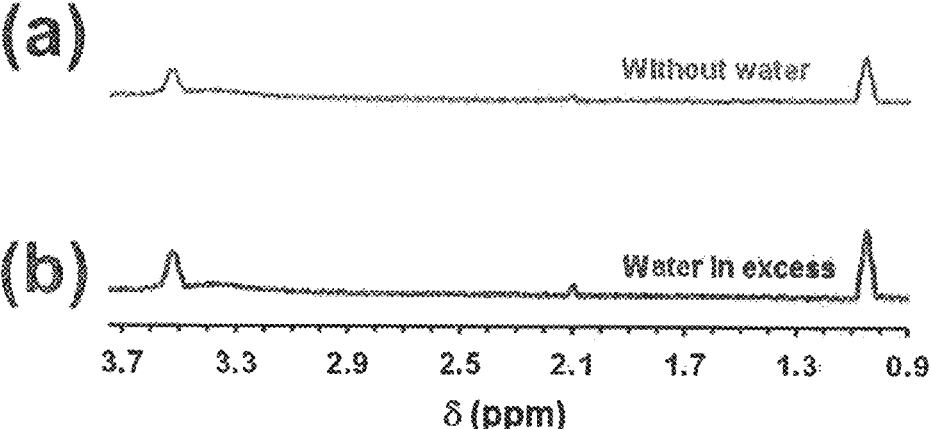
FIG. 9($a$) graphically shows the $^1$H-NMR spectrum of the reaction products achieved after 72 h from $CO_2$ (3 bar) and $CH_4$ (3 bar) at 95° C. using UV radiation and (uncoated) permanently polarized hydroxyapatite as catalyst in absence of water.

FIG. 9(a) graphically shows the $^1$H-NMR spectrum of the reaction products achieved after 72 h from $CO_2$ (3 bar) and $CH_4$ (3 bar) at 95° C. using UV radiation and (uncoated) permanently polarized hydroxyapatite as catalyst in absence of water.

FIG. 9(b) graphically shows the $^1$H-NMR spectrum of the reaction products achieved after 72 h from $CO_2$ (3 bar) and $CH_4$ (3 bar) at 95° C. using UV radiation and (uncoated) permanently polarized hydroxyapatite as catalyst with an excess of water.

FIG. 10 graphically shows the $^1$H-NMR spectrum of the solution obtained after extraction of the reaction products achieved after 72 h from polluted air (atmospheric pressure) and $H_2O$ (1 mL) at 95° C. using (uncoated) permanently polarized hydroxyapatite as catalyst at 95° C. and under UV radiation. The reacted catalyst was dissolved in an aqueous solution with 100 mM HCl and 50 mM NaCl.

FIG. 11(a) graphically shows a further $^1$H-NMR spectrum of the liquid water after reaction for 48 h from $CO_2$ (6 bar) and $H_2O$ (1 mL) using (uncoated) permanently polarized hydroxyapatite as catalyst and 140° C. as reaction conditions (without UV radiation). Spectra were cut to avoid the very intense peak of water at 4.7 ppm.

FIG. 11(b) graphically shows a further $^1$H-NMR spectrum of a solution obtained after extraction of the reaction products achieved after 48 h from $CO_2$ (6 bar) and $H_2O$ (1 mL) using (uncoated) permanently polarized hydroxyapatite as catalyst and 140° C. as reaction conditions (without UV radiation). The catalyst was dissolved in an aqueous solution with 100 mM HCl and 50 mM NaCl. Spectra were cut to avoid the very intense peak of water at 4.7 ppm.

The spectra reveal the apparition of methanol, formic acid, ethanol, acetic acid and acetone as reaction products in both the liquid water and the catalyst and the liquid water. The yields (μmol/g of catalyst) in the liquid water were: 0.21±0.07 (methanol), 2.44±0.97 (formic acid), 4.50±0.91 (ethanol), 2.22±0.88 (acetic acid) and 0.74±0.15 (acetone). The yields (μmol/g of catalyst) in the catalyst were: 0.56±0.19 (methanol), 3.22±0.54 (formic acid), 6.60±2.32 (ethanol), 0.49±0.12 (acetic acid) and 0.62±0.27 (acetone).

FIG. 12(a) graphically shows the variation of the yield (expressed as μmol of product/g of catalyst) of ethanol (EtOH), acetic acid (AcOH), methanol (MeOH), formic acid (HCOOH) and acetone (Ace) against the $CO_2$ pressure (in bars) as determined by $^1$H NMR spectroscopy from the solution obtained after extraction of the reaction products achieved after 48 h using $CO_2$ (1, 2, 4 or 6 bars) and $H_2O$ (1 mL) at 140° C. (without UV radiation). The catalyst was dissolved in an aqueous solution with 100 mM HCl and 50 mM NaCl.

FIG. 12(b) graphically shows the variation of the yield (expressed as μmol of product/g of catalyst) of ethanol (EtOH), acetic acid (AcOH), methanol (MeOH), formic acid (HCOOH) and acetone (Ace) against the $CO_2$ pressure (in bars) as determined by $^1$H NMR spectroscopy from the liquid water using (uncoated) permanently polarized hydroxyapatite as catalyst. In all cases the reaction was conducted for 48 h using $CO_2$ (1, 2, 4 or 6 bars) and $H_2O$ (1 mL) at 140° C. (without UV radiation).

FIG. 12(c) graphically shows the variation of the sum of the yields (expressed as μmol of product/g of catalyst) achieved from the solution obtained after extraction of the reaction products from the catalyst (FIG. 12a) and the supernatant (FIG. 12b) for ethanol (EtOH), acetic acid (AcOH), methanol (MeOH), formic acid (HCOOH) and acetone (Ace) against the $CO_2$ pressure (in bars). In all cases the reaction was conducted for 48 h using $CO_2$ (1, 2, 4 or 6 bars) and $H_2O$ (1 mL) at 140° C. (without UV radiation).

FIG. 12(d) graphically shows the variation of the sum of the yields (expressed as μmol of product/g of catalyst) achieved from the solution obtained after extraction of the reaction products from the catalyst (FIG. 12a) and supernatant (FIG. 12b) for C1 (methanol and formic acid; MeOH+ HCOOH), C2 (ethanol and acetic acid; EtOH+AcOH) and C3 (acetone; Ace) against the $CO_2$ pressure (in bars). In all cases the reaction was conducted for 48 h using $CO_2$ (1, 2, 4 or 6 bars) and $H_2O$ (1 mL) at 140° C. (without UV radiation).

FIG. 13(a) graphically shows the variation of the yield (expressed as μmol of product/g of catalyst) of ethanol (EtOH), acetic acid (AcOH), methanol (MeOH), formic acid (HCOOH) and acetone (Ace) against the temperature (in ° C.) as determined by $^1$H NMR spectroscopy from the solution obtained after extraction of the reaction products achieved after 48 h using $CO_2$ (6 bars) and $H_2O$ (1 mL) at 95, 120 or 140° C. (without UV radiation). The catalyst was dissolved in an aqueous solution with 100 mM HCl and 50 mM NaCl.

FIG. 13(b) graphically shows the variation of the yield (expressed as μmol of product/g of catalyst) of ethanol (EtOH), acetic acid (AcOH), methanol (MeOH), formic acid (HCOOH) and acetone (Ace) against the temperature (in ° C.) as determined by $^1$H NMR spectroscopy from the liquid water using (uncoated) permanently polarized hydroxyapatite as catalyst. In all cases the reaction was conducted for 48 h using $CO_2$ (6 bars) and $H_2O$ (1 mL) at 95, 120 or 140° C. (without UV radiation).

FIG. 13(c) graphically shows the variation of the sum of the yields (expressed as μmol of product/g of catalyst) achieved from the solution obtained after extraction of the reaction products from the catalyst (FIG. 13a) and the supernatant (FIG. 13b) for ethanol (EtOH), acetic acid (AcOH), methanol (MeOH), formic acid (HCOOH) and acetone (Ace) against the temperature (in ° C.). In all cases the reaction was conducted for 48 h using $CO_2$ (6 bars) and $H_2O$ (1 mL) at 95, 120 or 140° C. (without UV radiation).

FIG. 13(d) graphically shows the variation of the sum of the yields (expressed as μmol of product/g of catalyst) achieved from the solution obtained after extraction of the reaction products from the catalyst (FIG. 13a) and supernatant (FIG. 13b) for C1 (methanol and formic acid; MeOH+ HCOOH), C2 (ethanol and acetic acid; EtOH+AcOH) and C3 (acetone; Ace) against the temperature (in ° C.). In all cases the reaction was conducted for 48 h using $CO_2$ (6 bars) and $H_2O$ (1 mL) at 95, 120 or 140° C. (without UV radiation).

FIG. 14(a) graphically shows the variation of the yield (expressed as μmol of product/g of catalyst) of ethanol (EtOH), acetic acid (AcOH), methanol (MeOH), formic acid (HCOOH) and acetone (Ace) against the reaction time (in hours) as determined by $^1$H NMR spectroscopy from the solution obtained after extraction of the reaction products achieved after 24, 48 and 72 h using $CO_2$ (6 bars) and $H_2O$ (1 mL) at 140° C. (without UV radiation). The catalyst was dissolved in an aqueous solution with 100 mM HCl and 50 mM NaCl.

FIG. 14(b) graphically shows the variation of the yield (expressed as μmol of product/g of catalyst) of ethanol (EtOH), acetic acid (AcOH), methanol (MeOH), formic acid (HCOOH) and acetone (Ace) against the time (in hours) as determined by $^1$H NMR spectroscopy from the liquid water using (uncoated) permanently polarized hydroxyapatite as catalyst. In all cases the reaction was conducted for 24, 48 or 72 h using $CO_2$ (6 bars) and $H_2O$ (1 mL) at 140° C. (without UV radiation).

FIG. 14(*c*) graphically shows the variation of the sum of the yields (expressed as μmol of product/g of catalyst) achieved from the solution obtained after extraction of the reaction products from the catalyst (FIG. 14*a*) and the supernatant (FIG. 14*b*) for ethanol (EtOH), acetic acid (AcOH), methanol (MeOH), formic acid (HCOOH) and acetone (Ace) against the time (in hours). In all cases the reaction was conducted for 24, 48 or 72 h using $CO_2$ (6 bars) and $H_2O$ (1 mL) at 140° C. (without UV radiation).

FIG. 14(*d*) graphically shows the variation of the sum of the yields (expressed as μmol of product/g of catalyst) achieved from the solution obtained after extraction of the reaction products from the catalyst (FIG. 14*a*) and supernatant (FIG. 14*b*) for C1 (methanol and formic acid; MeOH+ HCOOH), C2 (ethanol and acetic acid; EtOH+AcOH) and C3 (acetone; Ace) against the time (in hours). In all cases the reaction was conducted for 24, 48 or 72 h using $CO_2$ (6 bars) and $H_2O$ (1 mL) at 140° C. (without UV radiation).

FIG. 15 graphically shows the $^1$H-NMR spectrum of the solution obtained after extraction of the reaction products achieved after 72 h from polluted air (atmospheric pressure) and $H_2O$ (1 mL) at 95° C. using (uncoated) permanently polarized hydroxyapatite as catalyst at 95° C. and under UV radiation. The reacted catalyst was dissolved in an aqueous solution with 100 mM HCl and 50 mM NaCl.

EXPERIMENTAL SECTION

1. Materials

Calcium nitrate ($Ca(NO_3)_2$), diammonium hydrogen phosphate (($NH_4)_2HPO_4$; purity >99.0%) and ammonium hydroxide solution 30% ($NH_4OH$; purity: 28-30% w/w) were purchased from Sigma Aldrich. Ethanol (purity >99.5%) was purchased from Scharlab. All experiments were performed with milli-Q water.

2. Hydrothermal Synthesis of Hydroxyapatite (HAp)

15 mL of 0.5 M of $(NH_4)_2HPO_4$ in de-ionized water were added at a rate of 2 mL·$min^{-1}$ to 25 mL of 0.5 M of $Ca(NO_3)_2$ in ethanol (with pH previously adjusted to 10.5 using ammonium hydroxide solution) and left aging for 1 h. The whole process was performed under gentle agitation (150 rpm) and at room temperature. Hydrothermal treatment at 150° C. was applied using an autoclave Digestec DAB-2 for 24 h. The autoclave was allowed to cool down before opening. The precipitates were separated by centrifugation and washed with water and a 60/40 v/v mixture of ethanol-water (twice). After freeze-drying it for three days, the white powder obtained was sintered for 2 h at 1000° C. in air using the Carbolite ELF11/6W/301 furnace.

3. Thermally Stimulated Polarization Process (TSP)

Mechanical consistent discs of around 1.5 mm of thickness were obtained by pressing 150 mg of previously sintered HAp powder at 620 MPa for 10 min. Thermal polarization was done placing the HAp discs between two stainless steel (AISI 304) and applying 3 kV/cm at 1000° C. for 1 h with a GAMMA power supply at 1000° C. using the same laboratory furnace as mentioned above. The discs were allowed to cool down maintaining the applied electric potential for 30 minutes, and finally, all the system was powered off and left to cool overnight.

4. Characterization

Vibrational spectra for a structural fingerprint were obtained by a confocal Raman microscope available from Renishaw under the trademarks INVIA™ QONTOR®, equipped with a detector available from Renishaw under the trademark CENTRUS™, model 2957T2 and a 785 nm laser.

SEM images were obtained using a microscope available from Zeiss NEON 40™ equipped with a SEM column available from Zeiss under the trademark GEMINI™. HRTEM was performed in a microscope model 2010F available from Japan Electron Optics Laboratory equipped with a field emission electron source and operated at an accelerating voltage of 200 kV. The point-to-point resolution was 0.19 nm, and the resolution between lines was 0.14 nm. Samples were dispersed in an alcohol suspension in an ultrasonic bath, and a drop of the suspension was placed over a grid with holey-carbon film. Images were not filtered or treated by means of digital processing and they correspond to raw data. All $^1$H-NMR spectra were acquired with a spectrometer available from Bruker under the trademark AVANCE III™ model 400 operating at 400.1 MHz and accumulating sixty-four scans. The chemical shift calibration was carried out using tetramethylsilane as internal standard. The samples were dissolved in milli-Q water containing 100 mM of HCl and 50 mM NaCl with the final addition of deuterated water.

5. Computational Details

The 2×1×2 HAp supercell was chosen to build the (0001) facet for p-HAp. The latter was built by removing an $OH^-$ orthonormal to the surface from the HAp supercell, which was previously optimized at the chosen DFT level. Consequently, a +1 global charge was applied for all calculations except for those involving formate, unpaired spin being considered when necessary. The initial coordinates of HAp were optimized following the computational details provided below to unwind surface tensions. The plane waves approach implemented in the Quantum Espresso 4.6 suite of Open-Source computer codes was used. Calculations were performed at the PBE level of theory corrected with the Grimme three body dispersion potentials (PBE-D3), applying the default $C_6$ software coefficients. A kinetic energy cutoff for the wave functions of 40 Ry was employed. A k-point mesh of 3×3×1 was automatically generated. Instead, a Gamma-center 1×1×1 k-mesh was used for calculations of discrete molecules and a 7×7×7 k-mesh for the bulk HAp calculations. Geometry optimizations were performed using the conjugated gradient algorithm until both the energy and force variation between consecutive steps was below $10^{-3}$ a.u and $10^{-4}$ a.u, respectively. The energy at each step was optimized until the deviation from self-consistency was below $10^{-5}$ Ry. Adsorption energies were calculated according to the following process: A+S→AS*, where A is the adsorbate; S the surface and AS* the adsorbed state. The adsorption energy ($E_{ads}$) was expressed as $E_{ads}=E_{AS*}-(E_A+E_s)$.

6. Reaction Chamber

A high pressure stainless steel reactor, which was designed ad hoc, was used to perform all the reactions. In brief, the reactor was dotted with a manometer, an electric heater with a thermocouple and an external temperature controller. The reactor was also characterized by an inert reaction chamber coated with a perfluorinated polymer (Teflon, 120 mL), where both the catalyst and water were incorporated. The reactor was equipped with three independent inlet valves for the incorporation of gases and an outlet valve to recover the gaseous reaction products. A UV lamp (GPH265T5L/4, 253.7 nm) was also placed in the middle of the reactor to irradiate the catalyst directly, the lamp being protected by a UV transparent quartz tube. All surfaces were coated with a thin film of perfluorinated polymer (Teflon) in order to avoid any contact between the reaction medium and the reactor surfaces, in this way discarding other catalyst effects.

7. Synthesis of Coated p-HAp

Three-layered systems consisting of the successive deposition of aminotris(methylenephosphonic acid) (ATMP) and zirconium oxychloride (ZC) onto p-HAp were obtained by immersion in the corresponding aqueous solutions at room temperature for 5 h. In order to deposit a first ATMP layer, p-HAp was immersed into a 5 mM ATMP solution for 5 h. Subsequently, ZC was deposited onto the ATMP layered p-HAp by immersing the latter into a 5 mM $ZrOCl_2$ solution for 5 h. Finally, a second layer of ATMP was deposited on the ZC and ATMP layered p-HAp by immersing the latter into a 1.25 mM ATMP solution for 5 h.

8. Synthesis of Functionalized Organic Molecules having 1 to 3 Carbon Atoms Using Uncoated p-HAp as Catalyst Functionalized organic molecules having 1 to 3 carbon atoms were synthesized from $CO_2$ gas alone (1, 2, 4 or 6 bars) as well as from $CO_2$ and $CH_4$ gas mixture (3 bar each) in the presence of uncoated p-HAp as catalyst and in the presence of liquid $H_2O$ (1 mL). The reaction was carried out for 24, 48 or 72 h at 95, 120 or 140° C. and under irradiation of an UV lamp (GPH265T5L/4, 253.7 nm) illuminating directly the uncoated p-HAp or without UV radiation.

As representative examples of reactions, the following yields (expressed as µmol of product per gram of catalyst) were obtained:

Reaction conducted for 72 h using $CO_2$ (3 bar), $CH_4$ (3 bar) and $H_2O$ (1 mL) at 95° C. under UV radiation.

Yields obtained from the solution obtained after extraction by dissolving the catalyst: ethanol (19.4±3.8 µmol/g), acetone (0.9±0.1 µmol/g) and acetic acid (0.6±0.1 µmol/g). Methanol and formic acid were not detected.

Yields obtained from the liquid water (supernatant): ethanol (0.7±0.14 µmol/g), acetic acid (2.0±0.5 µmol/g), methanol (1.5±0.3 µmol/g) and formic acid (1.9±0.6 µmol/g). Acetone was not detected.

Reaction conducted for 48 h using $CO_2$ (6 bar) and $H_2O$ (1 mL) at 140° C. without UV radiation.

Yields obtained from the solution obtained after extraction by dissolving the catalyst: ethanol (6.6±2.3 µmol/g), formic acid (3.2±0.5 µmol/g), acetone (0.6±0.3 µmol/g), methanol (0.6±0.2 µmol/g) and acetic acid (0.5±0.1 µmol/g).

Yields obtained from the liquid water (supernatant): ethanol (4.5±0.9 µmol/g), formic acid (2.4±1.0 µmol/g), acetic acid (2.2±0.9 µmol/g), acetone (0.7±0.1 µmol/g) and methanol (0.2±0.1 µmol/g).

Reaction conducted for 48 h using $CO_2$ (1 bar) and $H_2O$ (1 mL) at 140° C. without UV radiation.

Yields obtained from the solution obtained after extraction by dissolving the catalyst: acetone (1.6±0.6 µmol/g), formic acid (1.1±0.3 µmol/g), ethanol (0.8±0.2 µmol/g), acetic acid (0.8±0.2 µmol/g) and methanol (0.5±0.2 µmol/g).

Yields obtained from the liquid water (supernatant): acid acetic (2.4±1.0 µmol/g), formic acid (1.3±0.3 µmol/g), acid formic (1.1±0.3 µmol/g), acetone (0.8±0.3 µmol/g), ethanol (0.8±0.1 µmol/g) and methanol (0.1±0.03 µmol/g).

Reaction conducted for 48 h using $CO_2$ (6 bar) and $H_2O$ (1 mL) at 95° C. without UV radiation.

Yields obtained from the solution obtained after extraction by dissolving the catalyst: formic acid (1.1±0.3 µmol/g), ethanol (0.7±0.3 µmol/g), acetone (0.6±0.2 µmol/g), acetic acid (0.5±0.1 µmol/g) and methanol (0.3±0.1 µmol/g).

Yields obtained from the liquid water (supernatant): acid acetic (4.6±0.6 µmol/g), acetone (2.3±0.3 µmol/g), formic acid (1.1±0.1 µmol/g), and ethanol (0.4±0.1 µmol/g). Methanol was not detected.

Reaction conducted for 72 h using $CO_2$ (6 bar) and $H_2O$ (1 mL) at 140° C. without UV radiation.

Yields obtained from the solution obtained after extraction by dissolving the catalyst: ethanol (10.2±3.0 µmol/g), formic acid (2.4±0.5 µmol/g), acetone (0.9±0.2 µmol/g), acetic acid (0.7±0.2 µmol/g) and methanol (0.6±0.2 µmol/g).

Yields obtained from the liquid water (supernatant): ethanol (7.0±1.1 µmol/g), acetic acid (3.0±1.2 µmol/g), formic acid (1.9±0.8 µmol/g), acetone (1.1±0.4 µmol/g) and methanol (0.2±0.1 µmol/g).

9. Synthesis of Functionalized Organic Molecules having 1 to 3 Carbon Atoms Using Coated p-HAp as Catalyst Functionalized organic molecules having 1 to 3 carbon atoms were synthesized from $CO_2$ and $CH_4$ gas mixture (3 bar each) in the presence of coated p-HAp as catalyst and in the presence of liquid $H_2O$ (1 mL). The reaction was carried out for 72 h at 95° C. and under irradiation of an UV lamp (GPH265T5L/4, 253.7 nm) illuminating directly the coated p-HAp. The p-HA was coated with two layers of aminotris (methylenephosphonic acid) and a layer of zirconium oxychloride ($ZrOCl_2$), wherein the layer of zirconium oxychloride was arranged or sandwiched between the two layers of aminotris(methylenephosphonic acid). The yields (expressed as µmol of product per gram of coated p-HAp) obtained from the solution obtained after extraction by dissolving the catalyst were: ethanol (16.1±3.2 µmol/g), methanol (4.9±1.0 µmol/g), acetone (0.8±0.2 µmol/g) and acetic acid (0.6±0.1 µmol/g).

10. Synthesis of Ethanol Using Coated p-HAp as Catalyst

Ethanol was synthesized from $CO_2$ and $CH_4$ gas mixture (3 bar each) in the presence of coated p-HAp as catalyst and in the presence of liquid $H_2O$ (1 mL). The reaction was carried out for 72 h at 95° C. and under irradiation of an UV lamp (GPH265T5L/4, 253.7 nm) illuminating directly the coated p-HAp. The p-HA was coated with two layers of aminotris(methylenephosphonic acid) and a layer of zirconium oxychloride ($ZrOCl_2$), wherein the layer of zirconium oxychloride was arranged or sandwiched between the two layers of aminotris(methylenephosphonic acid). The reaction resulted in the following yields (expressed as µmol of product per gram of coated p-HAp): ethanol (16.1±3.2 µmol/g), methanol (4.9±1.0 µmol/g), malonic acid (1.6±0.2 µmol/g), acetone (0.8±0.2 µmol/g) and acetic acid (0.6±0.1 µmol/g). The predominant product, ethanol, was identified by means of $^1$H-NMR spectroscopy not only by the quartet ($CH_2$) and the triplet ($CH_3$) at 3.53 ppm and 1.06 ppm, respectively, but also by the intense OH peak at 4.65 ppm.

11. Synthesis of Ethanol Using (Uncoated) HAp as Catalyst

Ethanol was synthesized from $CO_2$ and $CH_4$ gas mixture (3 bar each) in the presence of (uncoated) HAp as catalyst and in the presence of liquid $H_2O$ (1 mL). The reaction was carried out for 72 h at 95° C. and under irradiation of an UV lamp (GPH265T5L/4, 253.7 nm) illuminating directly the p-HAp. The reaction resulted in a very poor yield of ethanol (1.9±0.5 µmol/g catalyst). Further, the yield of acetone and acetic acid was <0.1 µmol/g catalyst.

12. Synthesis of Ethanol without a Solid Support Acting as Catalyst

Ethanol was synthesized from $CO_2$ and $CH_4$ gas mixture (3 bar each) in the presence of (uncoated) HAp as catalyst and in the presence of liquid $H_2O$ (1 mL). The reaction was carried out for 72 h at 95° C. and under irradiation of an UV lamp (GPH265T5L/4, 253.7 nm). In absence of any solid support acting as catalyst (see FIG. 7(a)), the yield of ethanol is practically 0 (0.1±0.05 μmol/g). Such a small amount, which has been attributed to eventual photo-induced $CO_2$ reduction and water splitting, completely disappears in absence of UV radiation (see 7(b)).

13. Synthesis of Functionalized Organic Molecules having 1 To 3 Carbon Atoms, in Particular Ethanol, Using Traffic Contaminated Air As a proof of concept the reaction for synthesizing ethanol was conducted at atmospheric pressure using contaminated air taken from the surrounding area of the UPC (Universitat Politècnica de Catalunya) east campus in Barcelona, an area heavily contaminated by car traffic, since it is in front of one of the main roads of the city. The contaminated air by combustion of fossil carburant contains significantly higher $CO_2$ and $CH_4$ than the average of the ambient air. The reaction was conducted using p-HAp as catalyst, in presence of 1 mL of water and at 95° C. with UV radiation. Analysis of the reaction products after 72 h showed ethanol among other products, some of them non-identified in previous reactions with controlled gas mixtures. Despite the fact that the amount of ethanol (1.1±0.2 μmol/g), acetic acid (0.03±0.01 μmol/g), acetone (0.09±0.02 μmol/g), formic acid (0.13±0.05 μmol/g) and methanol (0.16±0.04 μmol/g) were very small, it was found the formation of high-value chemical products confirming the potential applicability of p-HAp as catalyst to regenerate contaminated air while obtaining functionalized organic molecules having 1 to 3 carbon atoms as valuable products.

14. Further Investigations in Terms of the Mechanism Pathway

The formation of functionalized organic molecules having 1 to 3 carbon atoms might be associated to the pressure of the feeding gas, the temperature and the reaction time. In order to explore the role of the reaction conditions, the process without UV illumination at was repeated using $CO_2$ gas and uncoated p-HAp as catalyst. As shown in FIGS. 12(a)-(d), the yield of functionalized organic molecules having 1 to 3 carbon atoms increases with pressure. The total yield (sum of the yields obtained for each product by dissolving the catalyst+sum of the yields obtained for each product from the supernatant) increased from 11.9±1.6 to 23.1±2.3 μmol/g when the pressure increases from 1 to 6 bars.

In summary, it could be confirmed the catalytic activity of permanently polarized hydroxyapatite to convert gaseous $CO_2$ in high-value organic chemicals, namely functionalized organic molecules having 1 to 3 carbon atoms, following an electro-reduction mechanism. Experiments under different reaction conditions reflect the formation of functionalized organic molecules having 1 to 3 carbon atoms, which are formed through the permanently polarized hydroxyapatite induced electro-reduction of $CO_2$. As a proof of concept, the proposed reaction has been successful in obtaining high-value chemical products from road traffic contaminated air, opening an exciting new avenue to transform greenhouse gas emissions into valuable chemical products using a simple catalyst based on an earth-abundant mineral.

The invention claimed is:

1. A process for producing functionalized organic molecules having 1 to 3 carbon atoms selected from the group consisting of ethanol, methanol, formic acid, acetic acid, malonic acid, acetone and a mixture of at least two of the afore-said functionalized organic molecules, the process comprising the step of:

contacting carbon dioxide as the only gas or a gas mixture comprising or consisting of carbon dioxide and methane in the presence of water with a catalyst comprising or consisting of permanently polarized hydroxyapatite, wherein the gas mixture is free of nitrogen.

2. The process according to claim 1, wherein the permanently polarized hydroxyapatite has:

a crystallinity >65% and/or a proportion of amorphous calcium phosphate <18% by weight, based on the total weight of the permanently polarized hydroxyapatite, and/or a proportion of β-tricalcium phosphate <36% by weight, based on the total weight of the permanently polarized hydroxyapatite, and/or a bulk resistance from $10^7$ Ω cm² to $10^5$ Ω cm², wherein the bulk resistance increases by only 4% to 73% after 3 months, and/or a surface capacitance decreasing less than 8% after 3 months.

3. The process according to claim 1, wherein the permanently polarized hydroxyapatite is obtained by a process comprising the steps of:

(a) preparing samples of hydroxyapatite, (b) sintering the samples prepared in step (a) at a temperature between 700° C. and 1200° C., (c) applying a constant or variable DC voltage between 250 V and 2500 V to the samples obtained in step (b) or to shaped bodies thereof or applying an equivalent electric field between 1.49 kV/cm and 15 kV/cm to the samples obtained in step (b) or to shaped bodies thereof or applying an electrostatic discharge between 2500 V and 1500000 V to the samples obtained in step (b) or to shaped bodies thereof or applying an equivalent electric field between 148.9 kV/cm and 8928 kV/cm to the samples obtained in step (b) or to shaped bodies thereof and (d) cooling the samples obtained in step (c) maintaining the DC voltage or the equivalent electric field or cooling the samples obtained in step (c) maintaining or without maintaining the electrostatic discharge or the equivalent electric field.

4. The process according to claim 1, wherein the permanently polarized hydroxyapatite is obtained by a process comprising the steps of:

(a) preparing samples of hydroxyapatite, (b) sintering the samples prepared in step (a) at a temperature between 700° C. and 1200° C., (c) applying a constant or variable DC voltage between 250 V and 2500 V for at least 1 minute at a temperature between 900° C. and 1200° C. to the samples obtained in step (b) or to shaped bodies thereof or applying an equivalent electric field between 1.49 kV/cm and 15 kV/cm for at least 1 minute at a temperature between 900° C. and 1200° C. to the samples obtained in step (b) or to shaped bodies thereof or applying an electrostatic discharge between 2500 V and 1500000 V for less than 10 minutes at a temperature between 900° C. and 1200° C. to the samples obtained in step (b) or to shaped bodies thereof or applying an equivalent electric field between 148.9 kV/cm and 8928 kV/cm for less than 10 minutes at a temperature between 900° C. and 1200° C. to the samples obtained in step (b) or to shaped bodies thereof and (d) cooling the samples obtained in step (c) maintaining the DC voltage or the equivalent electric field or cooling the samples obtained in step (c) maintaining or without maintaining the electrostatic discharge or the equivalent electric field.

5. The process according to claim 1, wherein the permanently polarized hydroxyapatite is obtained by a process comprising the steps of:
   (a) preparing samples of hydroxyapatite,
   (b) sintering the samples prepared in step (a) at a temperature of 1000° C.,
   (c) applying an equivalent electric field of 3 kV/cm at a temperature of 1000° C. to the samples obtained in step (b) or to shaped bodies thereof and
   (d) cooling the samples obtained in step (c) maintaining the equivalent electric field.

6. The process according to claim 1, wherein the permanently polarized hydroxyapatite is obtained by a process comprising the steps of:
   (a) preparing samples of hydroxyapatite,
   (b) sintering the samples prepared in step (a) at a temperature of 1000° C. for 2 h,
   (c) applying an equivalent electric field of 3 kV/cm at a temperature of 1000° C. for 1 h to the samples obtained in step (b) or to shaped bodies thereof and
   (d) cooling the samples obtained in step (c) maintaining the equivalent electric field for 30 minutes.

7. The process according to claim 1, wherein the contacting step is carried out in the presence of liquid water.

8. The process according to claim 1, wherein the contacting step is carried out with a volumetric ratio of the permanently polarized hydroxyapatite to water of 1000:1 to 0.01:1.

9. The process according to claim 1, wherein the contacting step is carried out with a volumetric ratio of carbon dioxide to methane of 200:1.

10. The process according to claim 1, wherein the contacting step is carried out under a total pressure of 0.1 bar to 100 bar.

11. The process according to claim 1, wherein the contacting step is carried out under a pressure of carbon dioxide of 0.035 bar to 100 bar.

12. The process according to claim 1, wherein the contacting step is carried out under a partial pressure of carbon dioxide of 0.035 bar to 90 bar.

13. The process according to claim 1, wherein the contacting step is carried out with a molar ratio of carbon dioxide to permanently polarized hydroxyapatite of 0.1 to 0.5 and/or with a molar ratio of methane to permanently polarized hydroxyapatite of 0.1 to 0.5.

14. The process according to claim 1, wherein the contacting step is carried out under UV irradiation or UV-Vis irradiation having a wavelength from 200 nm to 850 nm.

15. The process according to claim 1, wherein the contacting step is carried out under UV irradiation and/or Visible light irradiation having an irradiance from 0.1 W/m² to 200 W/m².

16. The process according to claim 1, wherein the contacting step is carried out at a temperature of 25° C. to 250° C.

17. The process according to claim 1, wherein the process is used for producing ethanol or a mixture comprising or consisting of ethanol and at least one further functionalized organic molecule selected from a group consisting of methanol, formic acid, acetic acid, malonic acid and acetone, or a mixture comprising or consisting of ethanol, methanol, formic acid, acetic acid and acetone or a mixture comprising or consisting of ethanol, methanol, acetic acid, malonic acid and acetone.

18. The process according to claim 1, wherein the process is used for removing carbon dioxide from the atmosphere.

* * * * *